US006185739B1

(12) United States Patent
Verkic et al.

(10) Patent No.: US 6,185,739 B1
(45) Date of Patent: Feb. 13, 2001

(54) LIGHT SHIELDING HELMET SYSTEM

(75) Inventors: Ivan Verkic; Hans G. Schiebold, both of Victoria (AU)

(73) Assignee: Comweld Group Pty. Ltd., Victoria (AU)

(*) Notice: Under 35 U.S.C. 154(b), the term of this patent shall be extended for 0 days.

(21) Appl. No.: 09/180,539

(22) PCT Filed: Mar. 13, 1998

(86) PCT No.: PCT/AU98/00170

§ 371 Date: Nov. 9, 1998

§ 102(e) Date: Nov. 9, 1998

(87) PCT Pub. No.: WO99/08637

PCT Pub. Date: Feb. 25, 1999

(30) Foreign Application Priority Data

Aug. 12, 1997 (AU) .................................................. P08526

(51) Int. Cl.⁷ ........................................................ A61F 9/06
(52) U.S. Cl. .............................................................. 2/8
(58) Field of Search ................................ 2/7, 8, 9, 424

(56) References Cited

U.S. PATENT DOCUMENTS

| D. 322,493 | 12/1991 | Metzger | D29/9 |
|---|---|---|---|
| D. 324,588 | 3/1992 | Metzger | D29/9 |
| D. 355,053 | 1/1995 | Honrud | D29/110 |
| D. 365,666 | 12/1995 | Gumpp | D29/110 |
| 2,270,028 | 1/1942 | Anderson | 2/8 |
| 2,628,530 | 2/1953 | Rabben | 88/41 |
| 3,251,065 | 5/1966 | Caldwell | 2/8 |
| 3,257,667 | 6/1966 | Anderson | 2/8 |
| 3,415,595 | 12/1968 | Nelson | 351/44 |
| 3,440,661 | 4/1969 | Newcomb | 2/14 |
| 3,444,561 | 5/1969 | Boyer | 2/8 |
| 3,577,563 | 5/1971 | Raschke | 2/8 |
| 4,101,979 | 7/1978 | Tarrone | 2/8 |
| 4,114,198 | 9/1978 | Sands | 2/8 |
| 4,774,723 | 10/1988 | Ruck | 2/8 |
| 4,853,973 | 8/1989 | Boochard | 2/8 |
| 4,945,572 | 8/1990 | Rosen | 2/8 |
| 4,989,598 | 2/1991 | Berg et al. | 128/206.23 |
| 5,012,528 | 5/1991 | Pernicka et al. | 2/10 |
| 5,062,156 | 11/1991 | Siegal | 2/8 |
| 5,140,707 | 8/1992 | Johnson | 2/8 |
| 5,224,219 | 7/1993 | Edwards et al. | 2/8 |
| 5,533,206 | 7/1996 | Petrie et al. | 2/8 |
| 5,548,448 | 8/1996 | Wagner . | |
| 5,669,070 | 9/1997 | Bennett et al. | 2/8 |

FOREIGN PATENT DOCUMENTS

| 1661776 | 2/1978 | (AU) | 876/43.8 |
|---|---|---|---|
| 2225646 | 6/1990 | (GB) | 61/2 |
| WO8806030 | 8/1988 | (WO) . | |

OTHER PUBLICATIONS

Arcmaster Brochure, "Eagle Series Setting New Standards".
Cigweld Brochure, "Safety Equipment Product Guide," Mar., 1996.
Euromaski Brochure, "Euromaski®," 1996.
MORSAFE Brochure, "XP5 Distributor Price List," Aug., 1996.
Optrel Brochure (represented by Harris–Welco), "This Is How Safe Welding Should Be".
Hornell Speedglas Inc. Brochure, "Speedglas® 9000 Quick Notes for Lens & Helmet," 1997.
Hornell Speedglas Inc. Brochure, "Speedglas®".

Primary Examiner—Michael A. Neas
(74) Attorney, Agent, or Firm—Senniger, Powers, Leavitt & Roedel

(57) ABSTRACT

A light shielding helmet system includes a helmet shell (2) configured for placement on the head of a user and at least two interchangeable lens holders (8, 70) having different lens-holding configurations. Each lens holder holds one or more lens plates (12) and each can be releasably mounted on the helmet shell (2). The lens holders (8, 70) can be of different styles (e.g., flip up or fixed front) and/or hold lens plates (12) of different sizes.

38 Claims, 26 Drawing Sheets

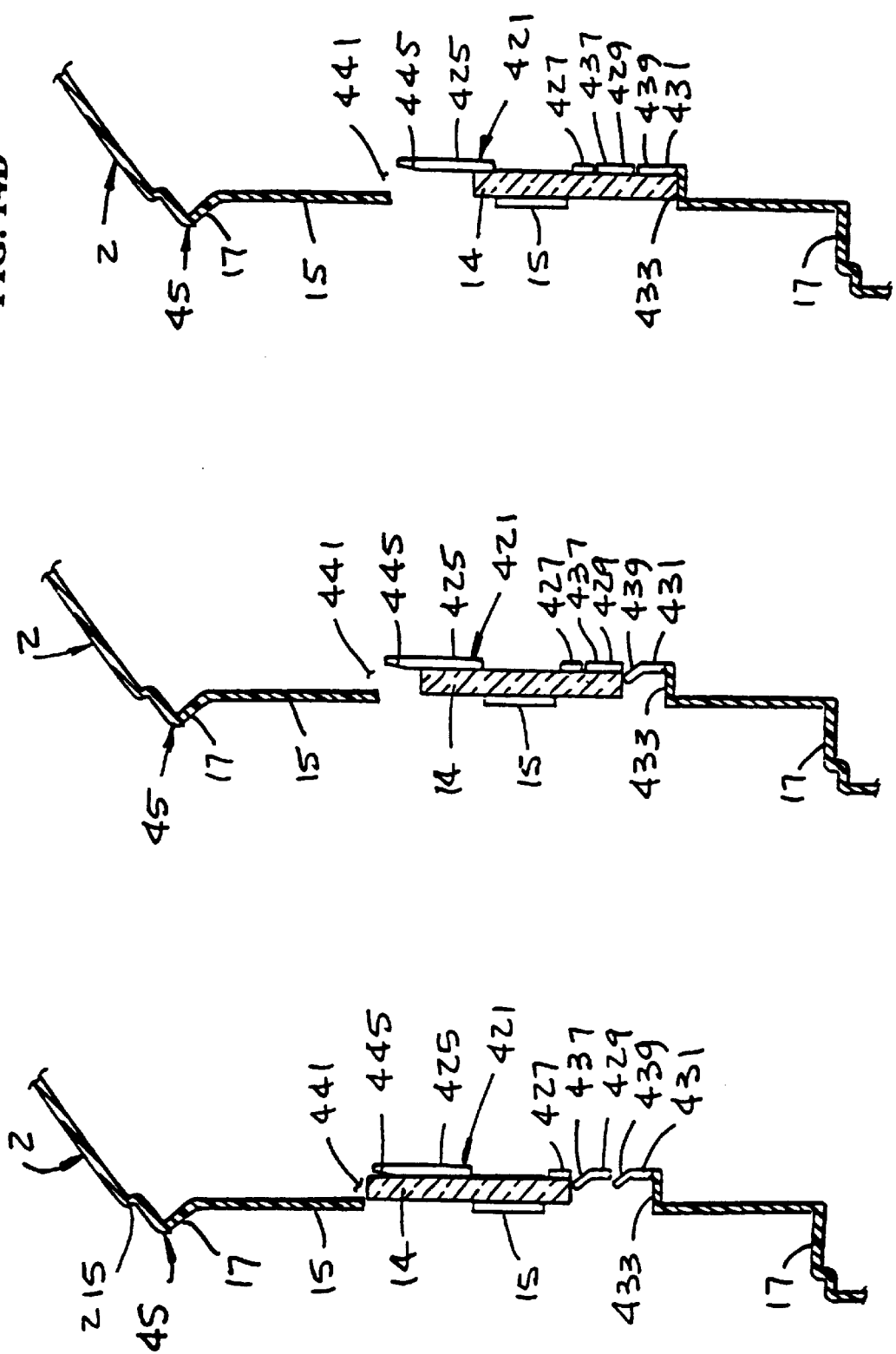

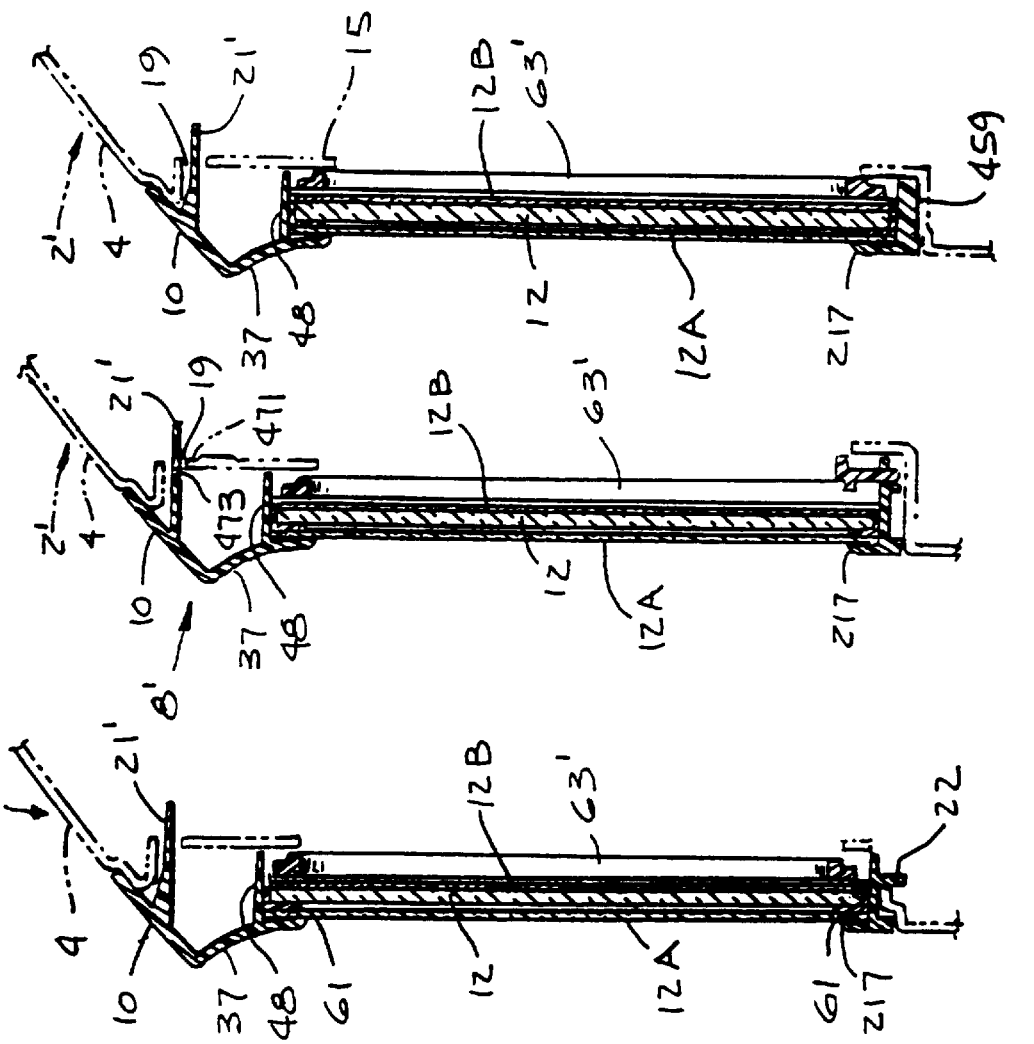

FIG. 15D
FIG. 15E
FIG. 15F
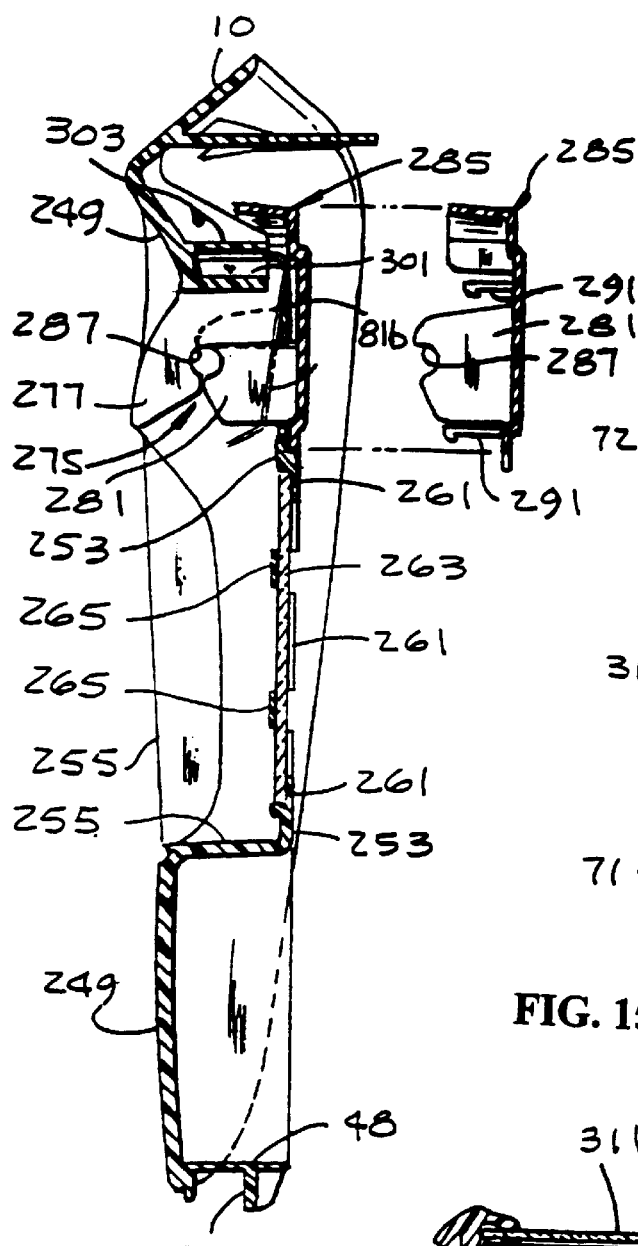
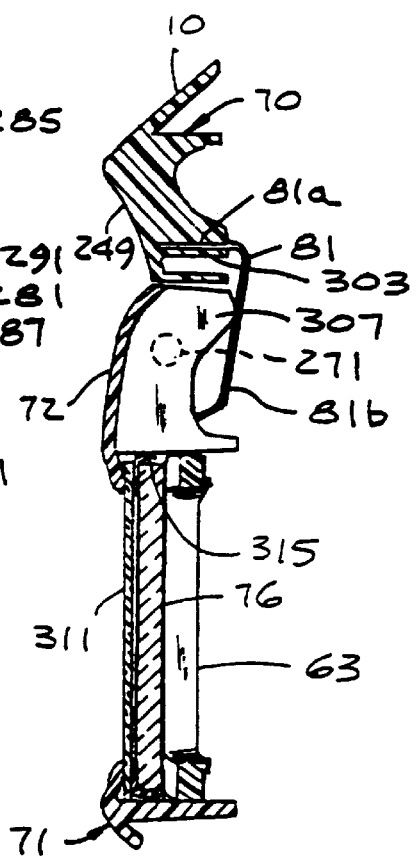
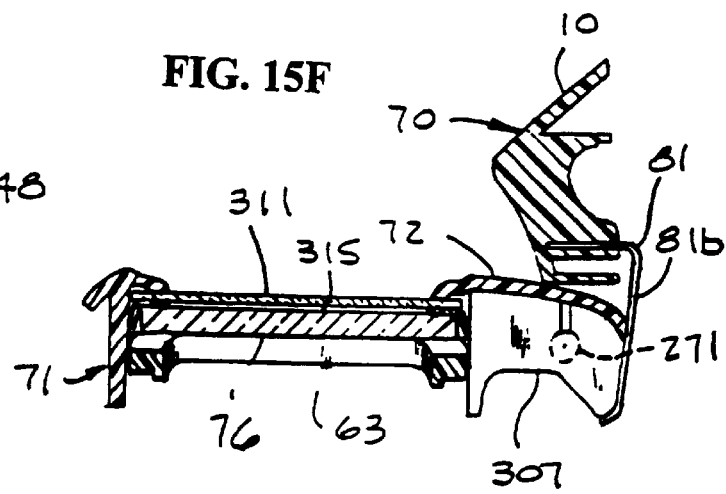

LIGHT SHIELDING HELMET SYSTEM

BACKGROUND OF THE INVENTION

The present invention relates to a light shielding helmet which includes a helmet shell and one or more lens assemblies to be mounted on the shell.

The invention has been developed primarily for use in welding operations and will be described hereinafter with reference to that application. It will be appreciated, however, that the invention is not limited to that particular field of use and is also applicable to helmets used during cutting or grinding operations, in metal production, or other applications where an operator using the helmet is subjected to high intensity radiation and particle splatter (e.g., molten metal fragments).

Many welding helmets are known. A common helmet includes a shell with a fixed lens for protecting the eyes of a user during a welding operation. It is also known to use a filter lens which automatically darkens in response to high intensity light from the welding operation, thereby attenuating that light to avoid damage to the user's eyes. In another known arrangement, referred to as a "lift front" helmet, the filter lens is moveable between filtering and non-filtering positions, and must be manually toggled between the two positions by the user in response to the timing of the steps of the welding operation. It is also known to releasably mount a lens cartridge to a helmet, such as that manufactured and sold by Hornell Elektrooptic AB and designated the Speedglas® 9000 helmet.

As will be understood by those skilled in the welding industry, different lens sizes are used for different welding applications and according to personal preference. For example, lens sizes of 133×144 mm (5×4 in.) and 83×108 mm (2×4 in.) are commonly used in the United States and Australia. Each lens size usually requires a helmet shell having a specific configuration. As a result, helmet shells of multiple configurations must be made and stocked. This increases the expense of manufacture because different helmet configurations require different tooling, the expense of distribution because multiple helmet configurations must be stocked, and user expense because more than one helmet configuration is typically required to meet different applications. Also, storing and handling multiple helmets is often inconvenient to the user.

Conventional welding helmets also have other drawbacks. For example, with respect to welding helmets having lift-front style lens holders, the pivoting frame carrying the filter lens typically includes an overcenter spring and cam mechanism which functions to urge the frame toward its up (non-filtering) and down (filtering) positions. Different helmets use different mechanisms but most involve the use of numerous separate parts. This increases production and assembly costs.

SUMMARY OF THE INVENTION

Among the several objects of the present invention is the provision of an improved welding helmet system which includes a helmet shell and multiple interchangeable lens holders which have different lens-holding configurations (e.g., 2×4 in. fixed front, 5×4 in. fixed front, 2×4 in. lift front) but which have the same mounting configuration so that the lens holders can be releasably mounted in interchangeable fashion on the same helmet shell; the provision of such a system which reduces manufacturing costs and the number of helmet shell configurations which need to be stocked; the provision of such a system which allows a user to use only one helmet shell for multiple lens sizes and styles; the provision of such a system which is designed so that the lens holders may be readily installed and removed; the provision of such a system in which each lens holder has a light-sealing fit with the helmet shell; the provision of such a system which is lightweight; the provision of such a system which allows for the convenient use and height adjustment of a magnifying ("mag") lens in the helmet; the provision of a welding helmet having a lift-front lens holder with an improved spring mechanism for urging the lens frame toward its filtering and non-filtering positions; the provision of such a spring mechanism which minimises the number of separate parts to reduce production and labor costs; the provision of such a spring mechanism which is easy to assemble; and the provision of such a spring mechanism which wears well for a longer life.

In a first aspect of this invention, a light shielding helmet system of the present invention comprises a helmet shell configured for placement on the head of a user. The helmet shell has an opening therein at a front of the shell for providing the user with a field of vision beyond the helmet, and a rim around the opening. A first lens holder is provided having a first lens-holding configuration for holding a first set of one or more lens plates, the first lens holder being releasably mountable on the helmet shell in a working position in which the first lens holder engages the rim of the helmet shell, in which the first lens holder is disposed in front of the opening in the helmet shell, and in which the one or more lens plates of the set are generally aligned with said opening. The system also includes a second lens holder having a second lens-holding configuration different from the lens-holding configuration of the first lens holder for holding a second set of one or more lens plates. The second lens holder is releasably mountable on the helmet shell in a working position in which the second lens holder engages the rim of the helmet shell, in which the second lens holder is disposed in front of the opening in the helmet shell, and in which the one or more lens plates of the second set are generally aligned with said opening. Each of the first and second lens holders has a mounting system which enables the lens holder to be mounted on the helmet shell so that the lens holders can be used interchangeably with the same helmet shell.

A second aspect of the invention involves a lens system separate and apart from the helmet shell. The system includes first and second lens holders of the type referred to above. The lens holders are configured so that they can be used interchangeably with the same single helmet shell.

A third aspect of this invention involves a light shielding helmet comprising a moulded plastic helmet shell configured for placement on the head of a user. The helmet shell has a front, top, opposite sides and an exterior surface, an opening in the front of the shell for providing the user with a field of vision beyond the helmet, and a rim projecting forward from the front of the shell around the opening. The rim has a top exterior surface and opposite side exterior surfaces recessed relative to the exterior surface of the helmet shell. The helmet also includes first and second lens plates, and a lens holder for holding the first and second lens plates generally parallel to one another with one plate behind the other. A mounting system is provided for releasably mounting the lens holder on the helmet shell in a working position in which the lens holder has a close fit with the rim of the helmet shell substantially to prevent the passage of light therepast, in which the lens holder is disposed in front of the opening in the helmet shell, and in which the lens plates held by the lens holder are generally aligned with the opening. The lens holder comprises a front panel having top, opposite sides and a bottom, and a peripheral skirt extending rearward from the front panel along its top and opposite sides. The front panel and skirt are formed as a moulded plastic unit, the skirt having a top, opposite sides and an exterior surface. The skirt of the lens holder is configured to be inserted over the top and opposite sides of the forwardly projecting rim of the helmet shell to mount the lens holder in its working position. The skirt of the lens holder is further configured to have an overlapping telescoping fit with the exterior surface of the rim so that the exterior surface of the skirt has a substantially flush fit with the exterior surface of the helmet shell to provide a smooth joint between the shell and the rim along the top and opposite sides of the rim.

A fourth aspect of this invention is directed to a helmet shell for a light shielding helmet in which the shell is configured for placement on the head of a user. The shell has an opening therein at a front of the shell for providing the user with a field of vision beyond the shell, a rim around the opening configured for mounting a lens holder in a position wherein the lens holder is in front of the opening and one or more lens plates held by the lens holder are generally aligned with the opening, and a mounting system on the helmet shell for mounting a magnifying lens plate in a plurality of different positions heightwise with respect to the opening in the shell whereby the heightwise position of the magnifying lens plate may be selectively varied.

This invention also involves a method of changing lens plates in a light shielding helmet of the type comprising a helmet shell configured for placement on the head of a user, an opening at a front of the shell for providing the user with a field of vision beyond the helmet, and a first lens holder having a first lens-holding configuration releasably mounted in a working position on the shell in front of the opening in the helmet shell. The lens holder holds a first pair of lens plates in general alignment with the opening in the helmet shell. The method comprises the steps of removing the first lens holder from the helmet shell, selecting a second lens holder having a second lens-holding configuration different from the lens-holding configuration of the first lens holder for holding a second pair of lens plates, and mounting the second lens holder on the helmet shell in said working position so that the second lens holder is disposed in front of the opening in the helmet shell and the lens plates of the second pair of lens plates are generally aligned with the opening in the helmet shell.

Another aspect of this invention is directed to a light shielding helmet comprising a helmet shell configured for placement on the head of a user. The helmet shell has an opening therein at a front of the shell for providing the user with a field of vision beyond the helmet. The helmet includes a lens holder comprising a panel releasably mounted on the helmet shell at the front of the shell and having an opening therein aligned with the opening in the helmet shell, and a frame mounted at the front of the panel for holding a filter lens plate. A pair of laterally spaced bearings on the panel mount the frame for pivotal movement about a pivot axis between a filtering position in which the filter lens plate is aligned with the openings in the helmet shell and panel, and a non-filtering position in which the filter lens plate is pivoted away from said openings. A leaf spring mechanism is also provided comprising at least one leaf spring mounted on one of the panel and the frame and at least one cam mounted on the other of the panel and the frame. The cam and leaf spring are engageable with one another as the frame is pivoted between said filtering and non-filtering position to urge the frame toward said filtering position when the frame is adjacent said filtering position and toward said non-filtering position when the frame is adjacent said non-filtering position.

Other objects and features of this invention shall be in part apparent and in part pointed out hereinafter.

BRIEF DESCRIPTION OF THE DRAWINGS

A preferred embodiment of the invention will be described, by way of examples only, with references to the accompanying drawings in which:

FIGS. 14B–14D are vertical sectional views illustrating a mag lens plate mounted at different elevations on the inside of the helmet shell of FIG. 14A;

FIG. 14I is a vertical sectional view taken on line 14I—14I of FIG. 14F;

FIG. 14J is a vertical sectional view taken on line 14J—14J of FIG. 14F;

FIG. 14K is a vertical sectional view taken on line 14K—14K of FIG. 14F;

FIG. 14L is a vertical sectional view taken on line 14L—14L of FIG. 14F;

FIG. 15D is a vertical section on line 15D—15D of FIG. 15B but with the lift-front frame removed show bearing means and the removable back wall portion of the lens holder;

FIG. 15E is a vertical section taken on line 15E—15E of FIG. 15B showing the lift-front frame in a down (filtering) position;

FIG. 15F is a partial view similar to FIG. 15E but showing the lift-front frame in a raised position;

Corresponding reference characters indicate corresponding parts throughout the drawings.

DETAILED DESCRIPTION OF PREFERRED EMBODIMENTS

Figure 1:
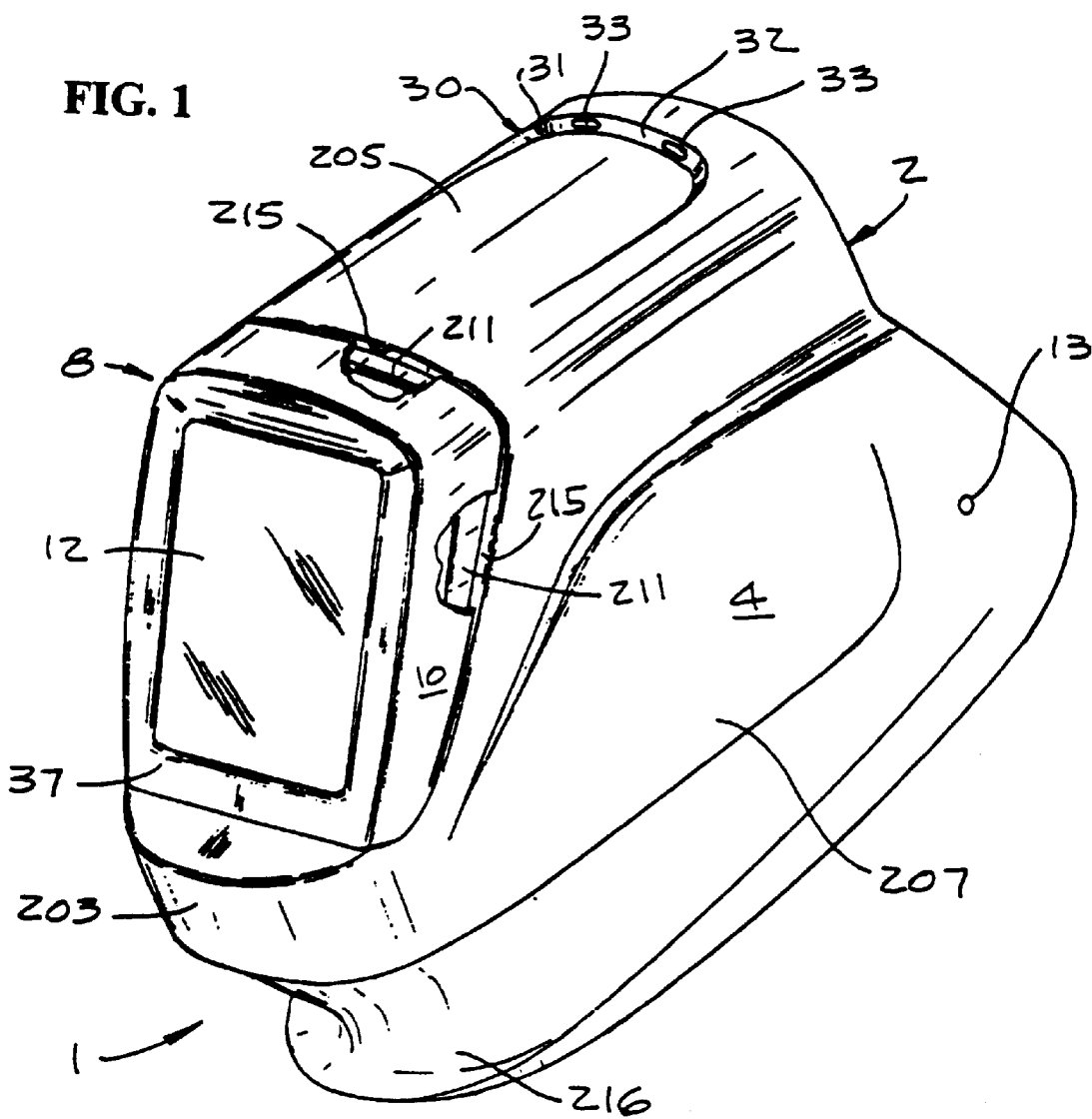
FIG. 1 is a perspective view of a helmet according to the invention.
Figure 2:
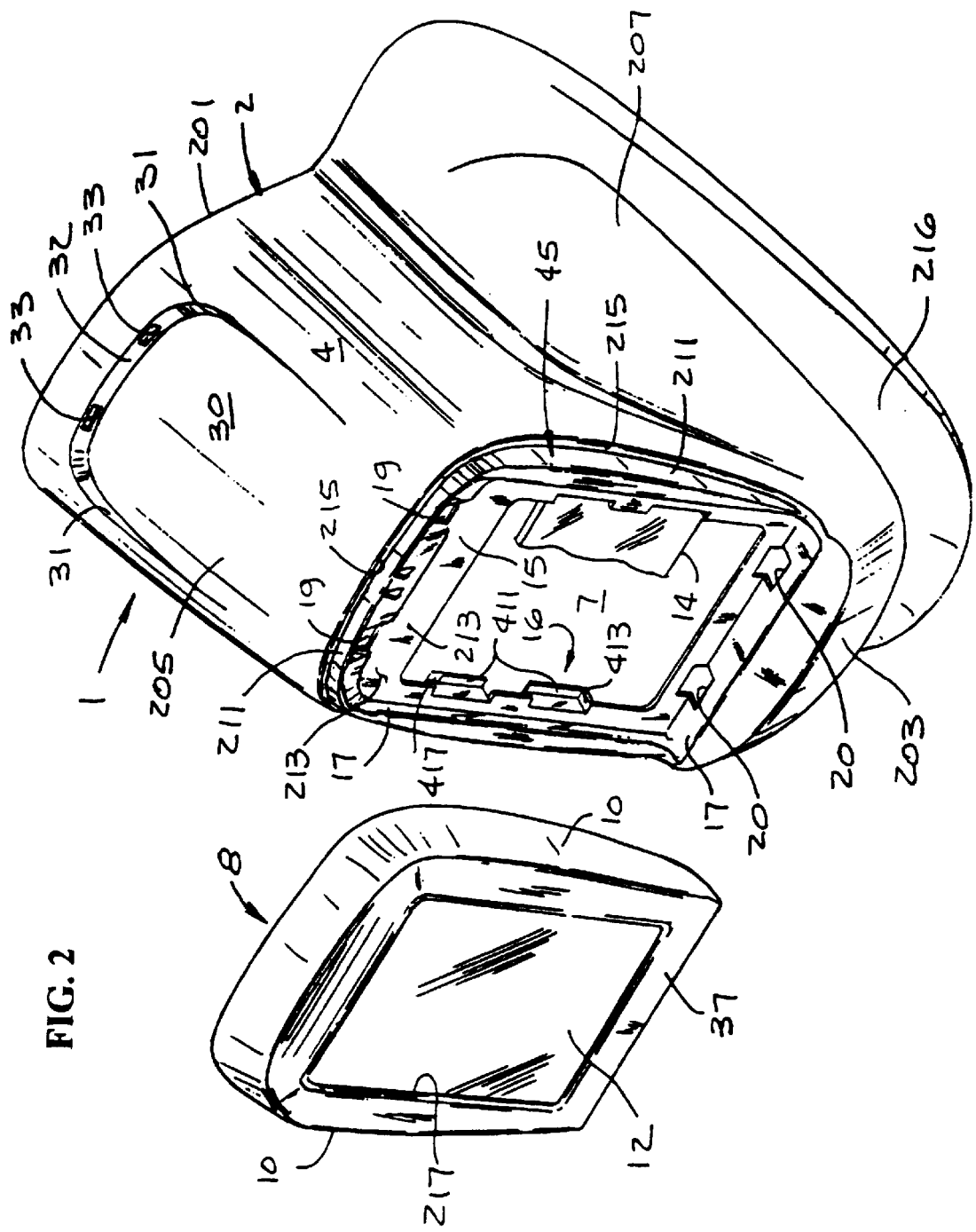
FIG. 2 is a perspective view of the helmet of FIG. 1 with the lens holder detached from the shell.
Figure 3:
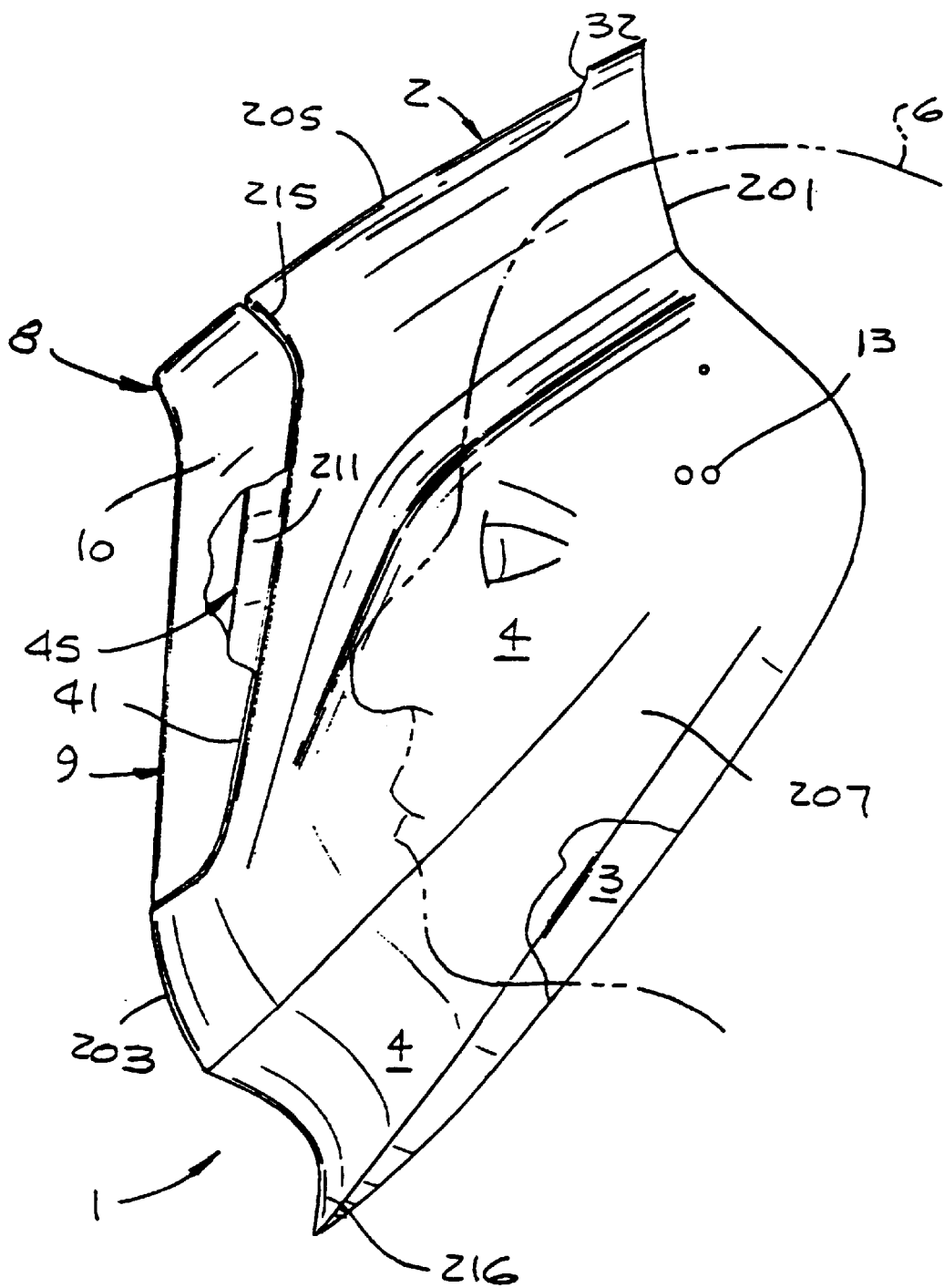
FIG. 3 is a side view of the helmet of FIG. 1 as worn by an operator (shown in Phantom) to illustrate relative placement of the helmet.
Figure 4:
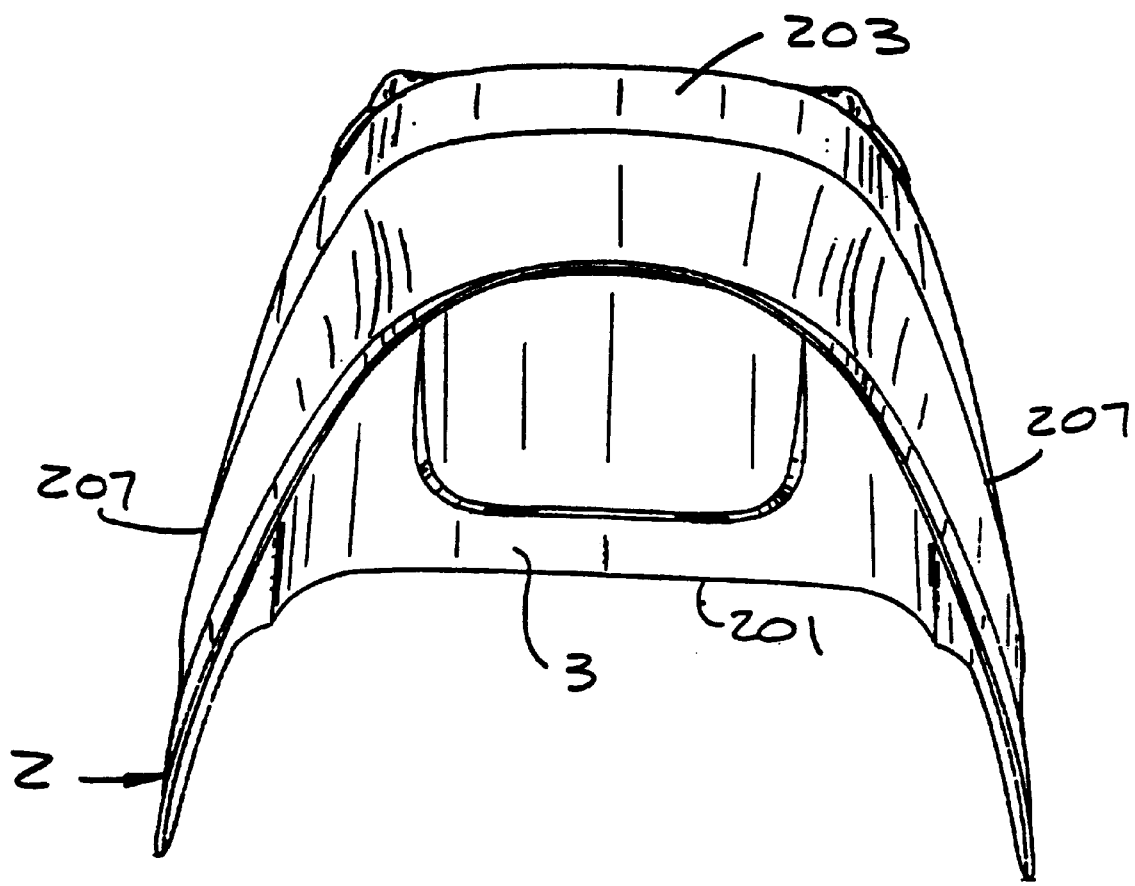
FIG. 4 is a bottom view of the helmet of FIG. 1.
Figure 5:
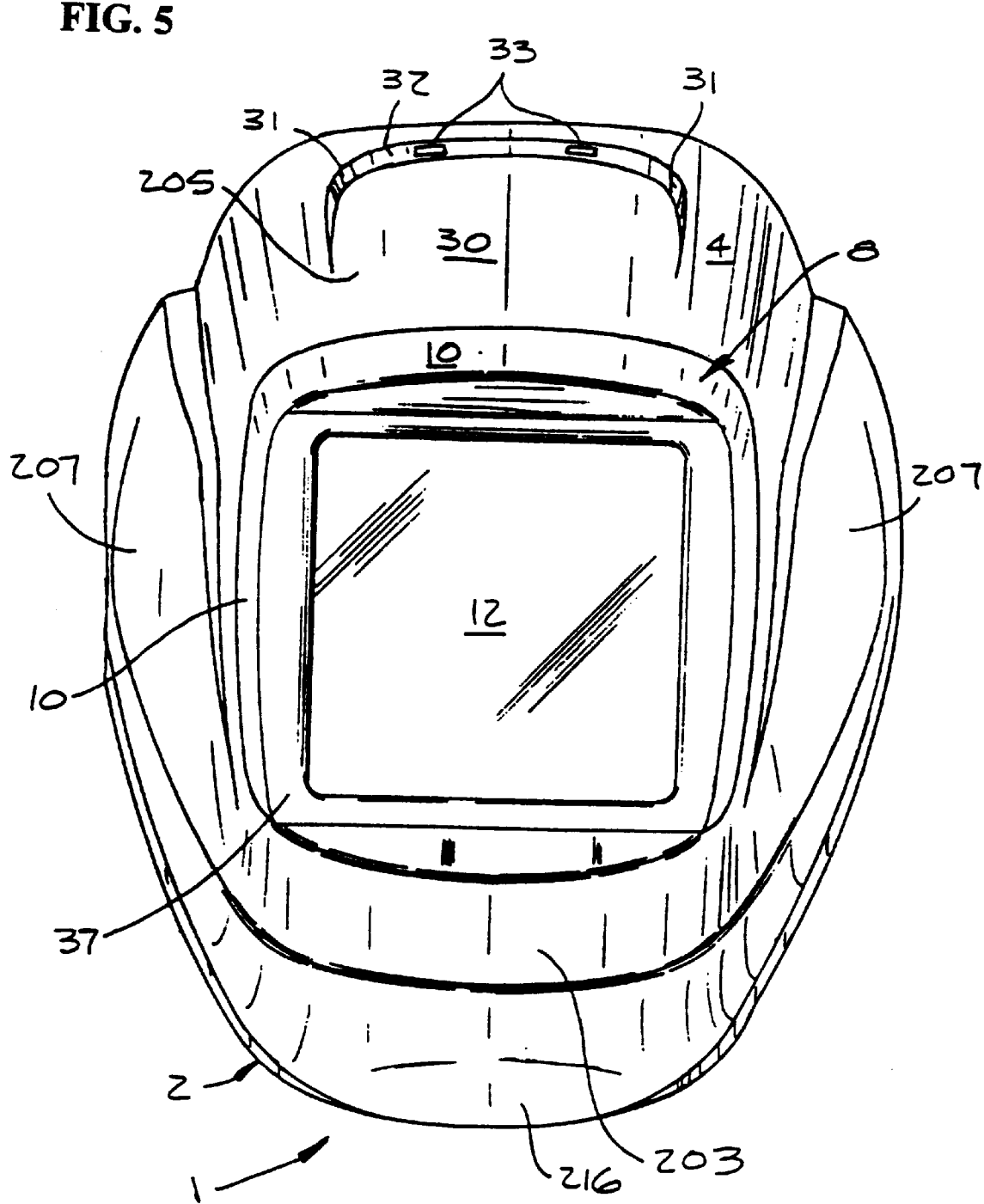
FIG. 5 is a front view of the helmet of FIG. 1.

Referring in particular to FIGS. 1 to 5, a light shielding helmet of the present invention is designated in its entirety by the reference numeral 1. As shown, the helmet includes a helmet shell generally designated 2 which is preferably an integrally moulded plastic part. The shell 2 has an open back 201, a front 203, a top 205, opposite sides 207, an inner (interior) surface 3 and an outer (exterior) surface 4. The interior surface 3 is configured for placement adjacent to a user's head 6, as best shown in FIG. 3. As will be appreciated by those skilled in the art, the shell 2 is suspended from the user's head by a harness, which for the purposes of clarity has been omitted from the drawings. The shell includes apertures 13 which provide mounting points for such a harness. The shell also includes a window opening 7 at the front of the shell for providing the user with a field of view beyond the helmet (see FIG. 2). A lens holder, generally designated 8, is releasably mounted on the shell 2 for providing a light seal around the window opening 7. As will be explained in more detail below, the lens holder 8 holds a set of one or more lens plates, including at least a filter lens plate 12 for reducing the intensity of light viewed by a person wearing the helmet. (The lens holder and lens plate(s) therein are sometimes referred to as a "lens cartridge".) The lens holder 8 depicted in FIGS. 1 and 2 has a lens-holding configuration known as a "fixed front" configuration sized for holding a 133×114 mm (5×4 in.) size lens plate. (As used herein, the "size" of a lens plate means its length and width dimensions, not the thickness of the lens.) As will be explained in detail hereinafter, lens holders having other lens-holding configurations may also be mounted on the helmet shell 2.

As best shown in FIG. 2, the window opening 7 in the helmet shell 2 is bounded by a flat support surface in the form of a platform 15 which extends around the opening. The platform provides a large surface against which the lens holder 8 rests when it is mounted on the shell 2. This provides for greater safety by preventing the lens holder from being pushed inwardly through the window opening and toward the face and/or eyes of the user.

The helmet shell 2 shown in FIG. 2 has a mounting system for mounting a magnifying ("mag") lens plate 14 behind the window opening 7. The system comprises a pair of support formations, each generally designated 16, formed as an integral part of the shell at opposite sides of the window opening 7 for supporting opposite ends of the mag lens plate in a position where the plate is immediately behind the opening and generally parallel thereto. (Only one support formation 16 is shown in FIG. 2.) Each support formation comprises coplanar back support surfaces 411 spaced rearward from and generally parallel to the platform 15, and a bottom surface 413. The back support surfaces 411 and platform 15 define slots at opposite sides of the window opening 7 for slidably receiving respective ends of the mag lens plate 14 so that the plate may be slidably moved to a position in which it rests on the bottom support surfaces 413. The spacing between surfaces 411 and platform 15 is preferably such as to provide a friction fit of the mag lens plate in respective slots sufficient to enable the mag plate to be readily installed while holding the mag lens plate securely in place. The uppermost back support surfaces 411 may be tapered at their upper ends as indicated at 417 to facilitate initial loading of the mag lens plate into the support formations 16. In other embodiments the magnifying lens is included within the lens holder 8 adjacent to lens 12.

Referring again to FIG. 2, a rim 45 projects forward from the front of the shell 2 around the window opening 7 and platform 15. The rim 45 has three outer (exterior) side walls 211 which merge with the exterior surface 4 of the shell along the top and opposite sides of the rim, and four inner (interior) side walls 17 which project forward from the platform 15 of the shell and define a rectangular recess 213 around the window opening 7 for receiving the lens holder 8. It will be understood that the rim 45 and recess 213 defined by the rim can take shapes other than the shape shown in the drawings without departing from the scope of this invention. The outer side walls 211 of the rim are recessed relative to the exterior surface 4 of the helmet shell 2 to provide a continuous step or shoulder 215 around the top and sides of the rim. (The reasons for this shoulder will become apparent later.)

The platform 15 and two inner side walls 17 of the rim 45 include respective mounting formations (fastening elements) in the form of apertures 19, 20 for receiving respective cooperable mounting formations 21 and 22

(fastening elements) on the lens holder 8. As will be explained hereinafter, fastening elements 19, 20, 21 and 22 constitute a mounting system for releasably mounting the lens holder 8 on the helmet shell 2.

The top of helmet 1 includes a recessed portion 30 defined by two opposed substantially parallel vertical walls 31 and a connecting wall 32 which extends normal to walls 31 (FIG. 2). The connecting wall 32 includes two spaced apart frangible tabs 33 which are selectively removed to provide apertures for receiving complementary attachment formations of an overhead shield (not shown). This shield is often in the form of a flexible burn resistant cloth which drapes down over the open back of the helmet 1 to protect the user's neck and/or shoulders from any weld spatter, sparks or other harmful emissions, such as molten metal, resulting from a welding or cutting operation. In other embodiments the shield is produced from a solid or less flexible material such as a thermoplastic.

The shield is particularly useful when overhead welding operations are carried out. In other embodiments other indents are provided at other locations in shell to facilitate connection of other shields to helmet 1. The shell has a lower extension 216 forming a neck and chest protector.

The lens holder 8 is illustrated in more detail in FIGS. 6 to 9. The holder comprises a front panel 37 having a top 38, a bottom 39, two opposite sides 40 and a large central rectangular lens opening 217 therein somewhat smaller in size than the filter lens plate 12 held by the holder 8. A peripheral skirt 10 extends rearward from the front panel 37 along its top 38 and opposite sides 40. The skirt and front panel of the holder are preferably of unitary moulded construction. The skirt is configured to have a close telescoping overlapping fit over the outer walls 211 of the forwardly projecting rim 45 at the top and sides of the rim. The skirt 10 has a wall thickness approximately equal to the height of the shoulder 215 and terminates in a continuous peripheral edge 41. When the lens holder 8 is mounted on the helmet shell 2, this edge 41 lies closely adjacent the shoulder 215 on the shell, the skirt being so configured that the outer exterior surface of the skirt has a substantially flush fit with the exterior surface 4 of the helmet shell to provide a smooth joint between the shell and the rim along the top and opposite sides of the rim for presenting a smooth, streamlined appearance (see FIGS. 3 and 10–14).

Figure 7:
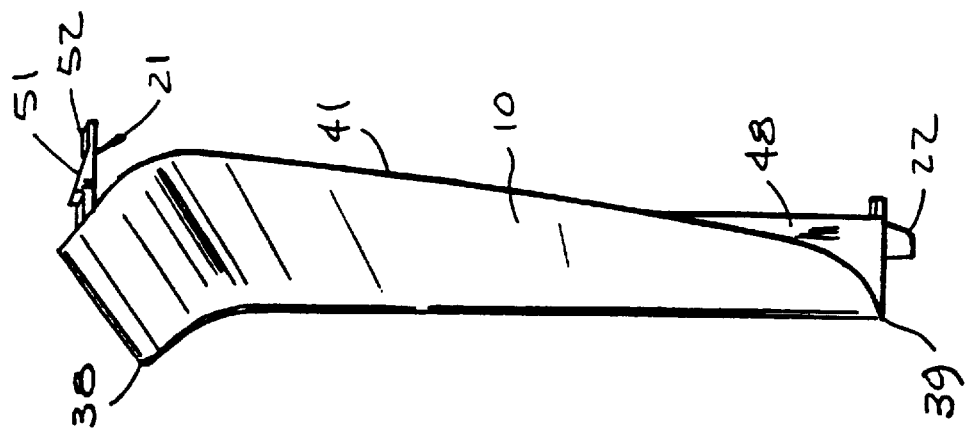
FIG. 7 is a side view of the lens holder of FIG. 6.
Figure 6:
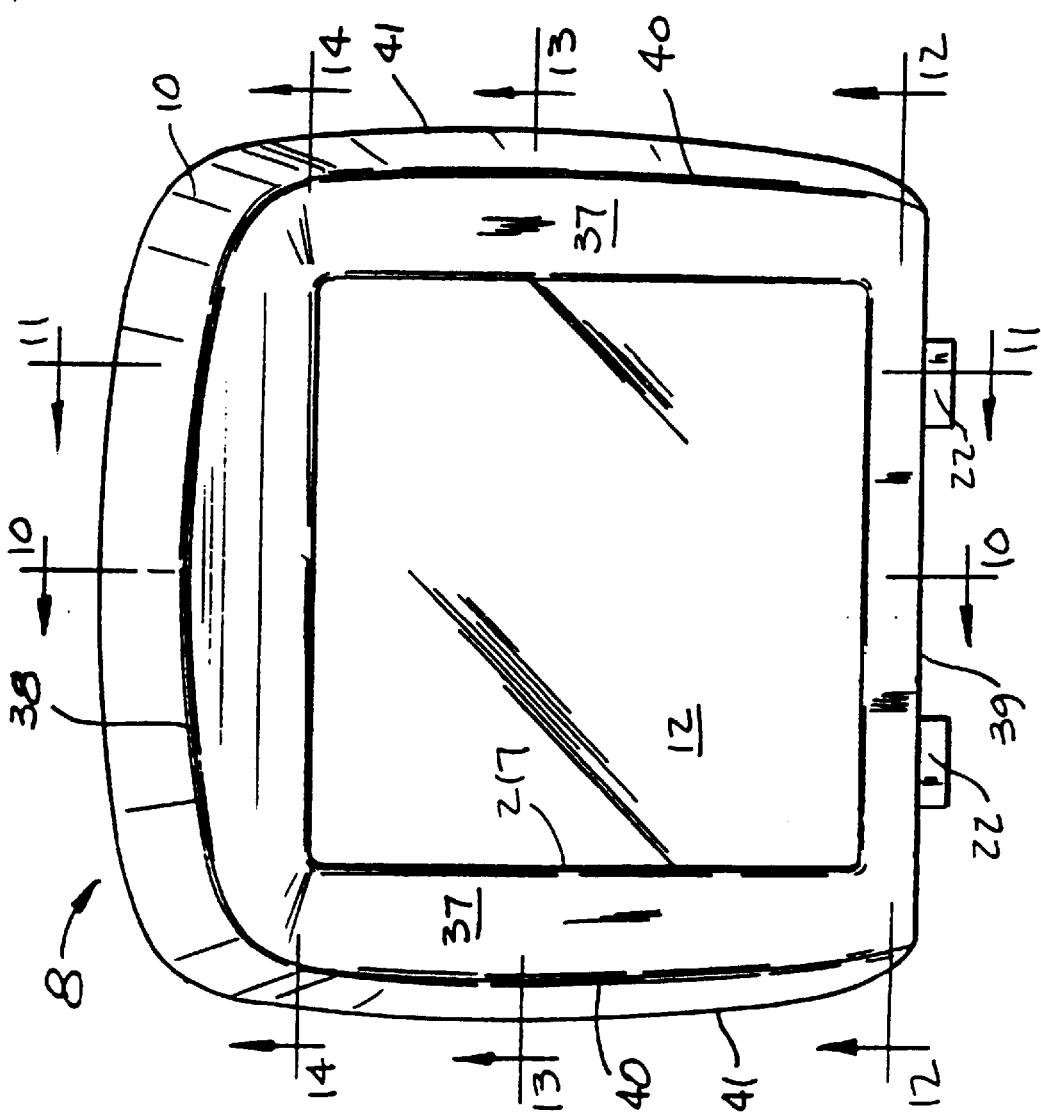
FIG. 6 is a front view of the lens holder of FIG. 1 removed from the helmet.
Figure 11:
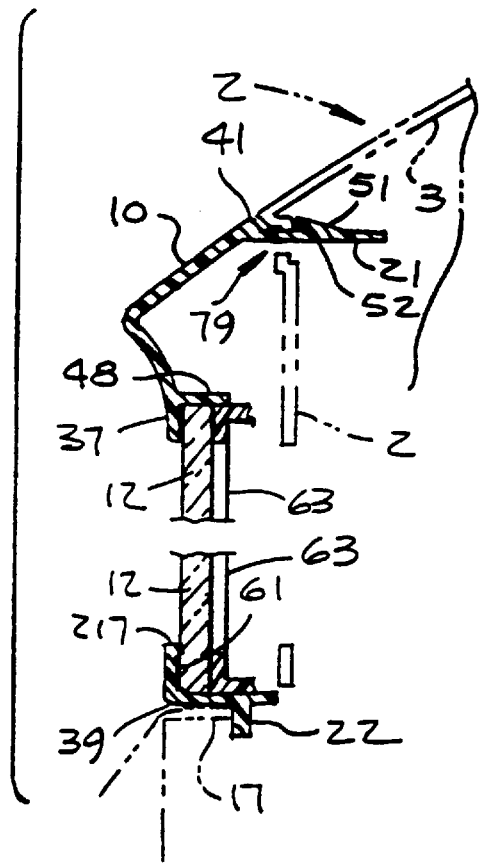
FIG. 11 is a vertical cross section taken along line 11—11 of FIG. 6 with adjacent portions of the helmet shell being shown by phantom lines.

The fastening elements 21, 22 on the lens holder 8 comprise a pair of flexible catches 52 extending rearwardly from the skirt 10 of the lens holder adjacent the top of the holder and a pair of lugs 22 adjacent the bottom 39 of the lens holder (see FIGS. 7 and 11). The catches 52 are receivable in the openings 19 in the platform of the helmet shell, and the lugs 22 are receivable in the openings 20 in the bottom side wall 17 of the rim 45 (see FIG. 2). Each catch 52 is formed with an inclined surface or ramp 51 which allows insertion of the catch into a respective aperture 19 in the platform 15 of the helmet shell, while simultaneously effecting resilient deformation of the catch. Once the catch 52 is received in the aperture, it returns to its resting configuration for snaplocking the catch into engagement with the shell 2 to fasten the holder in its working position on the shell. In this configuration forward and rearward movement of the lens holder 8 with respect to shell 2 is prevented. It will be understood that fastening elements 19, 20, 21 and 22 can be configured in other ways without departing from this invention, so long as the mounting system permits the holder 8 to be releasably attached to the shell 2.

Figure 10:
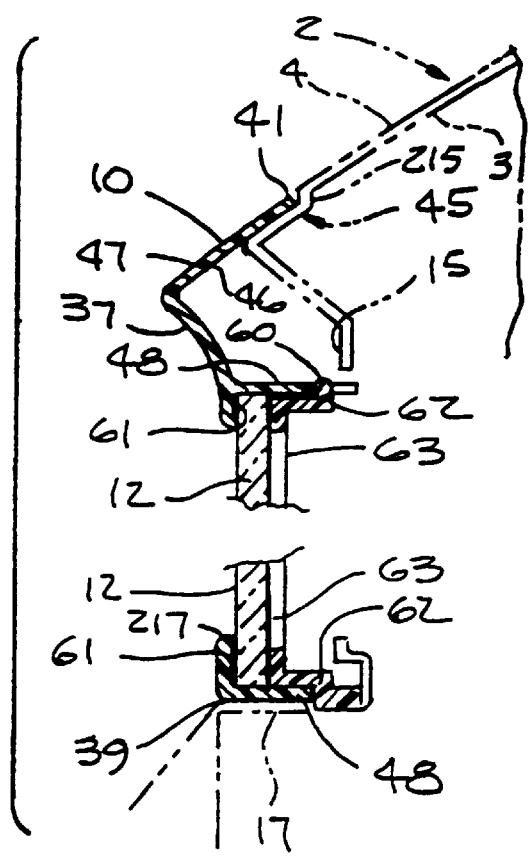
FIG. 10 is a vertical cross section taken along line 10—10 of FIG. 6 with adjacent portions of helmet shell being shown by phantom lines.
Figure 12:
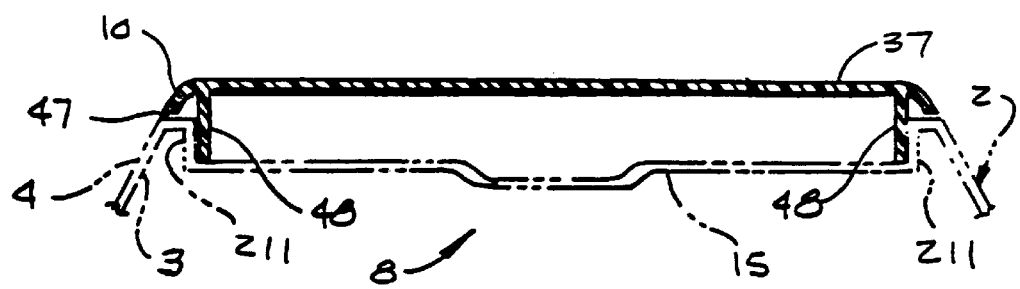
FIG. 12 is a horizontal cross section taken along line 12—12 of FIG. 6 with adjacent portions of helmet shell being shown by phantom lines.
Figure 13:
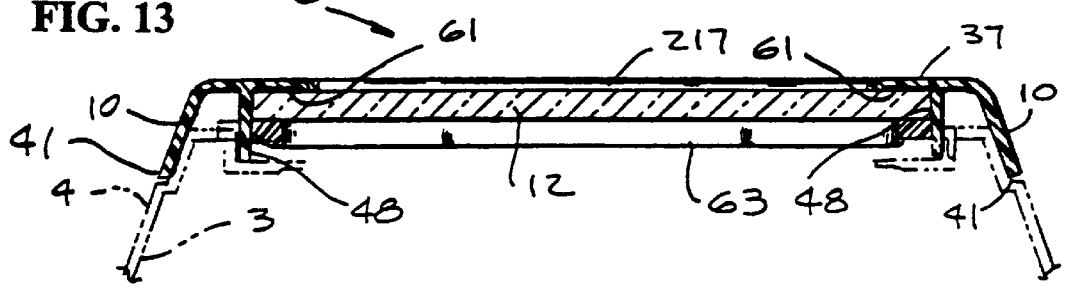
FIG. 13 is a horizontal cross section taken along line 13—13 of FIG. 6 with adjacent portion of the helmet shell being shown by phantom lines.
Figure 14:
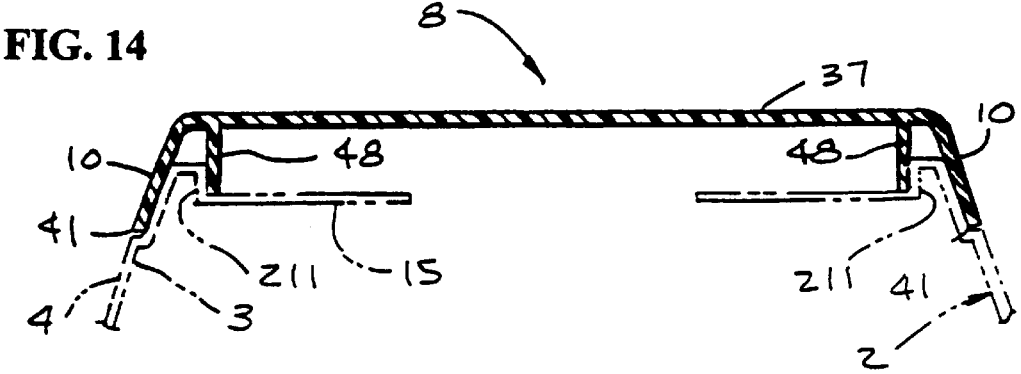
FIG. 14 is a horizontal cross section taken along line 14—14 of FIG. 6 with adjacent portion of the helmet shell being shown by phantom lines.

As shown best in FIGS. 9–14, a plurality of walls 48 extend rearward from the front panel 37 of the lens holder 8 and form a rectangular lens mount around and immediately to the rear of the lens opening 217 in the front panel. The lens mount is also formed by the rearwardly facing inner surface 61 of the front panel 37 bounding the lens opening 217, as shown in FIG. 10. The lens mount is sized for holding the filter lens plate 12 in alignment with the lens opening 217. When the lens holder 8 is mounted on the shell, the filter plate 12 held by the lens holder is aligned with the window opening 7 in the shell and positioned immediately forward thereof. Also, as shown in FIGS. 12–14, the walls 48 of the lens mount engage the sidewalls 211 and platform 15 of the shell to provide strong support.

The lens 12 is held in the lens mount in the position shown in FIG. 10 by a generally rectangular lens spring 63. The lens spring is retained in position by locating formations or projections 62 on the spring received in apertures 60 in the upper and lower walls 48 of the lens mount. The spring is engageable with the lens to bias the lens against the inner surface 61 of the front panel to a position in which the lens is aligned with the lens opening 217 in the lens holder. The lens spring 63 shares a large contact surface area with the lens and is advantageously secured centrally of the lens holder 8 within apertures 60 to reduce the risk of detachment.

Optionally, the lens holder 8 may hold a safety lens plate (not shown) of shatter resistant material immediately behind and aligned with the filter lens 12. The lens holder may also hold a cover lens plate (not shown) forward of the filter lens plate 12 to protect the filter plate. These lens plates have approximately the same length and width dimensions.

In use, the lens holder 8 is releasably mounted on the shell 2 so that it may be removed and replaced by a different lens holder. To effect mounting of the lens holder, the bottom 39 of the front panel 37 is rested against the bottom side wall 17 of the rim 45 such that the lugs 22 are inserted into corresponding apertures 20 in the side wall (FIG. 2). The lens holder is then rotated (pivoted) about its bottom 39 until the catches 52 snaplock into the apertures 19. To remove the lens holder, the free ends of the catches 52 are manually forced in a downward direction from inside helmet 1, and then pushed forward. Once the catches 52 have emerged from apertures 19 the downward force is no longer required.

FIG. 14A–14D shows a helmet shell 2' similar to shell 2, and FIGS. 14E–14M show a lens holder 8' similar to lens holder 8 for use with shell 2'. Corresponding parts of the shells 2, 2' and lens holders 8,8' are designated by the same reference numerals. Relevant differences between the shells 2 and 2' and the lens holders 8 and 8' are discussed below.

Figure 14A:
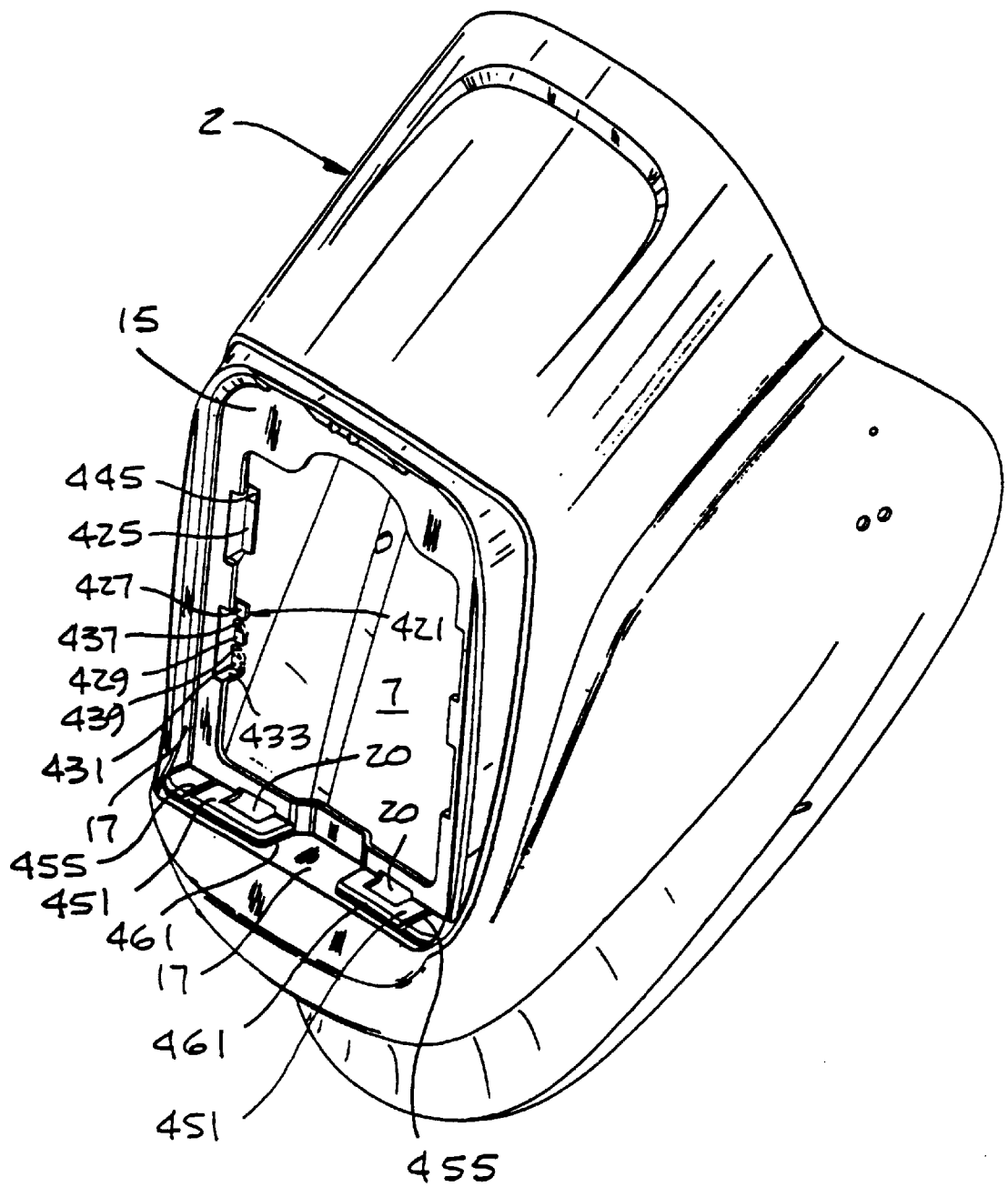
FIG. 14A is a perspective view of a helmet shell of alternative construction.
Figure 14E:
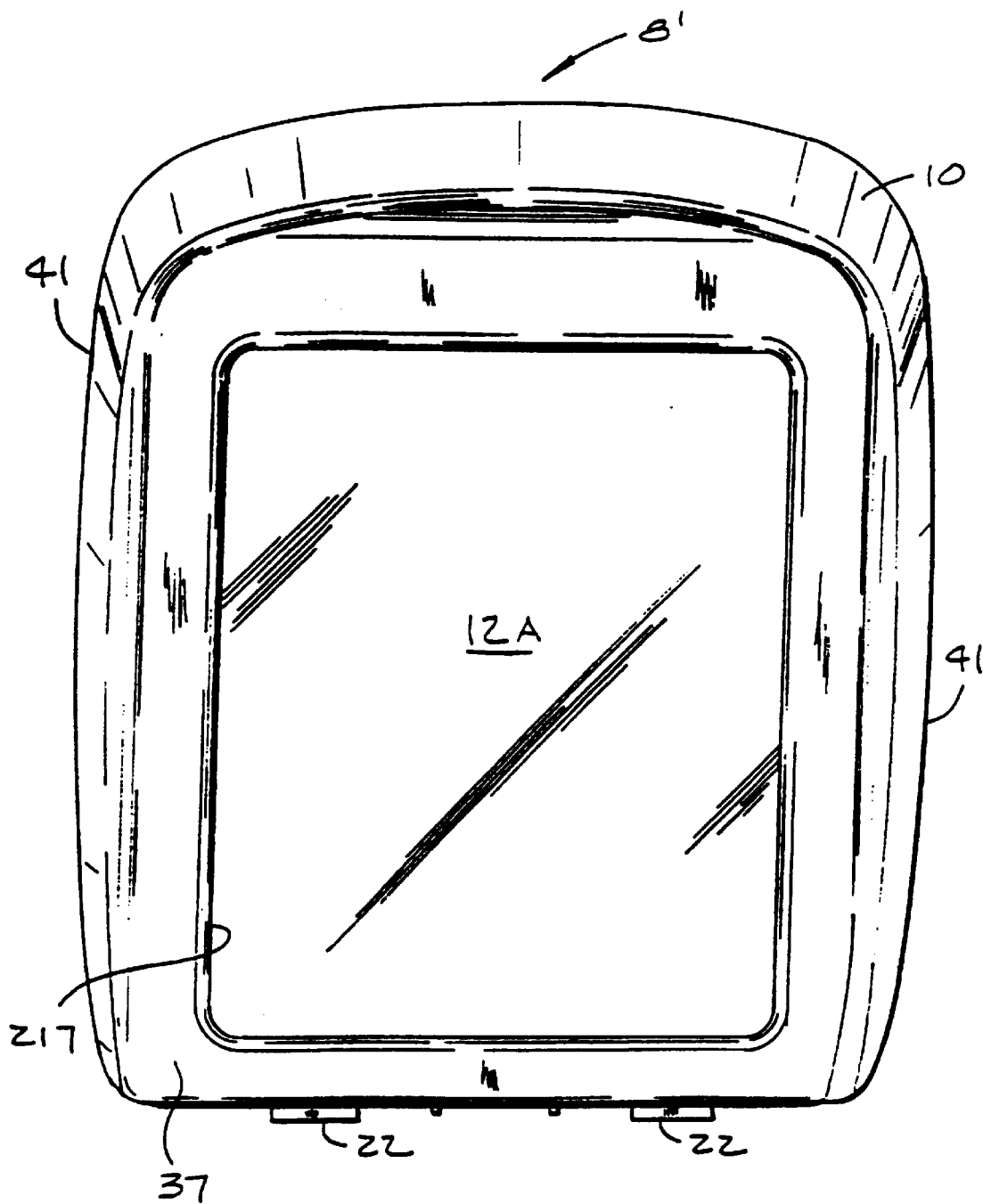
FIG. 14E is a front view of a lens holder of alternative construction.
Figure 14F:
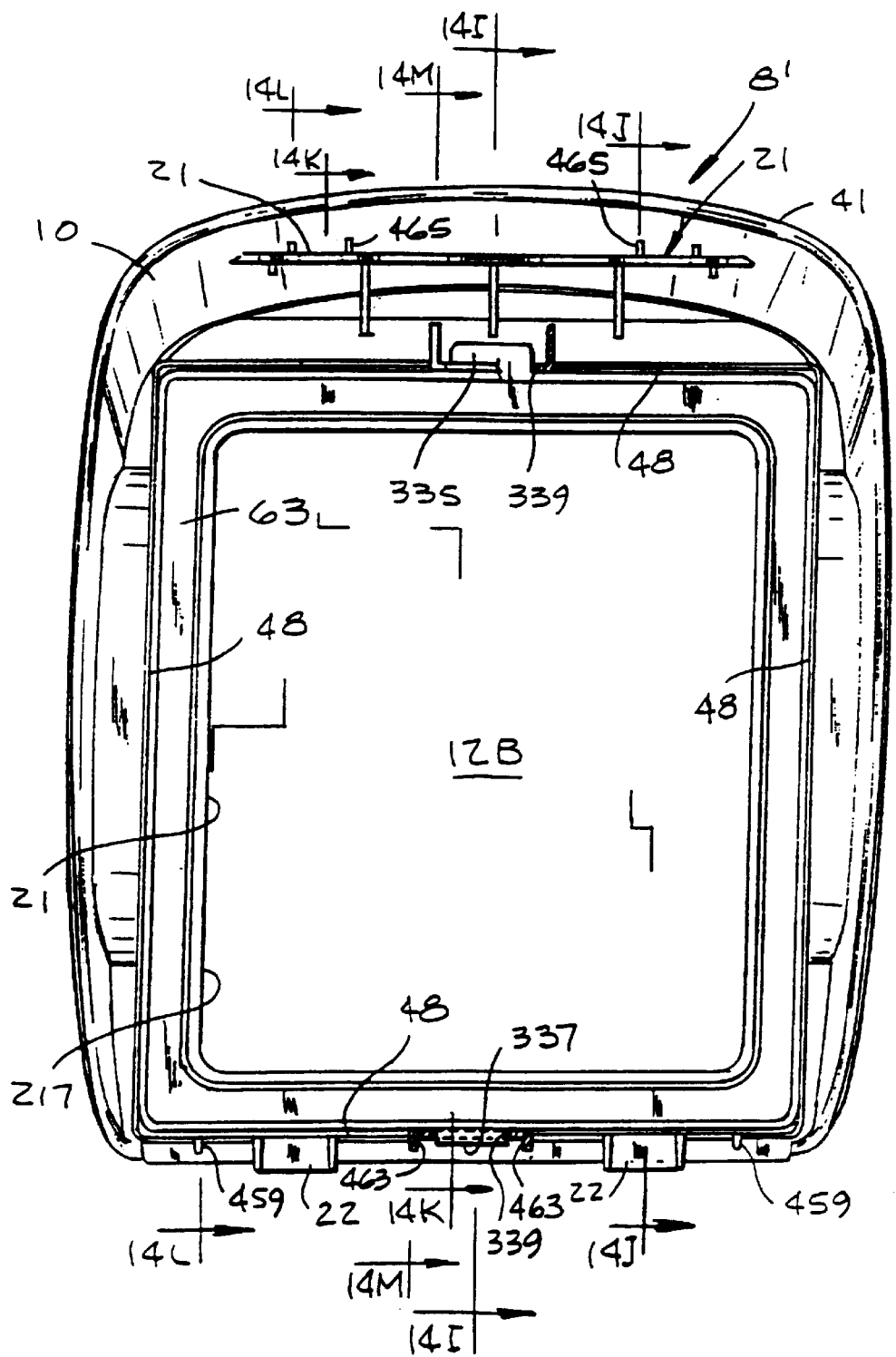
FIG. 14F is a rear view of the lens holder of FIG. 14E.

As shown in FIG. 14A, helmet shell 2' has a system for mounting a magnifying lens plate 14 behind the window opening 7 in a plurality different positions heightwise with respect to the opening, so that the heightwise position of the mag lens plate may be selectively varied, according to the type of work being performed and/or the preference of the person using the helmet and/or the lens configuration being used. The mounting system comprises a pair of support formations, each generally designated 421, formed as an integral part of the shell at opposite sides of the window opening 7 for supporting opposite ends of the mag lens plate 17 in a position where the plate is immediately behind the opening and generally parallel thereto. (Only one support formation 421 is shown in FIG. 14A.) Each support formation comprises coplanar back support surfaces 425, 427, 429 and 431 spaced rearward from and generally parallel to the platform 15, and a bottom support surface 433. A plurality of lens supports comprising resilient spring fingers 437 and 439 angle upward and forward from the upper ends of back support surfaces 429 and 431, respectively. The back support surfaces 425, 427, 429, 431 and platform 15 define a slot 441 (FIGS. 14B–14D) which slidably receives a respective end of the mag lens plate 14 so that the plate may be slidably moved to one of the three positions shown in FIGS. 14B–14D. In FIG. 14B, the mag lens plate is received in the slots 441 (one at each side of the window opening 7, although only one is shown) and rests on the upper spring fingers 437 (which constitute a first pair of lens supports) so that the plate is supported in a first, relatively elevated position with respect to the window opening 7. In FIG. 14C, the mag lens plate 14 rests on the lower spring fingers 439 (which constitute a second pair of lens supports) so that the plate is supported in a second, intermediate position with respect to the window opening 7. To place the mag lens plate in this position, the upper spring fingers 437 are sprung back to allow downward movement of the plate in the slots 441 past the fingers 437, following which the spring fingers press against the rear face of the plate. In FIG. 14D, the mag lens plate 14 rests on the bottom support surfaces 433 (which constitute a third pair of lens supports) so that the plate is supported in a third, lowermost position with respect to the window opening 7. The lower spring fingers 437 are sprung back to allow downward movement of the plate in the slots 441 from the intermediate position to the lowermost position. The spacing between surfaces 411 and platform 15 is preferably such as to provide a friction fit of the mag lens plate in respective slots sufficient to enable the mag plate to be readily installed while holding the mag lens plate securely in place. The uppermost back support surfaces 425 may be tapered at their upper ends as indicated at 445 to facilitate initial loading of the mag lens plate into the support formations 421.

The mag lens plate mounting system described above allows the user of the helmet to place the mag lens plate 14 in any preferred position. More or less spring fingers can be provided for supporting the plate at any number of different elevations. It will be understood that the particular configuration of the support formations 421 may vary without departing from the scope of this invention.

The helmet shell shown in FIG. 14A also includes an improved design for sealing against the entry of light into the helmet. More specifically, the bottom interior side wall 17 of the rim 45 has raised formations, each designated 451, around each aperture 20 to prevent the leakage of light therethrough when the holder 8 is in place on the shell. Each formation has a groove 455 in its upper surface located between its respective aperture 20 and a respective vertical interior side wall 17 of the rim. The grooves 455 extend in front-to-back direction with respect to the helmet shell and receive ribs 459 on the bottom of the lens holder 8' (see FIG. 14F) to provide light seals. The outer peripheries of the raised formations are chamfered as indicated at 461 for engagement by corresponding ribbing structure 463 on the bottom of the lens holder to complete the seal against passage of light through the apertures 20.

Figure 14G:
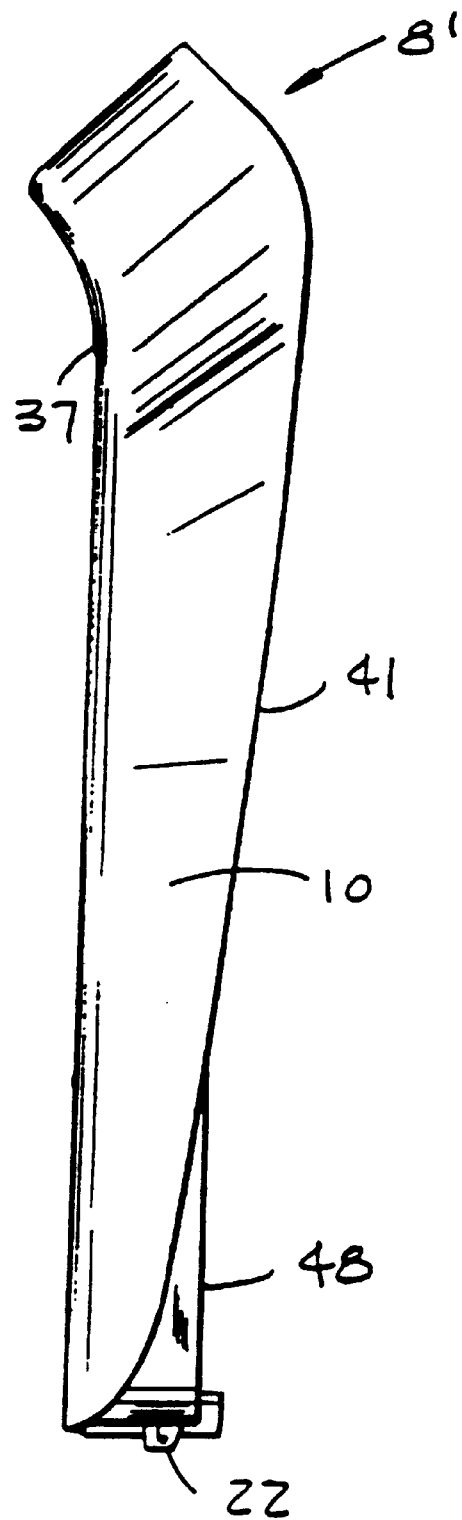
FIG. 14G is a side view of the lens holder of FIG. 14E.
Figure 14H:
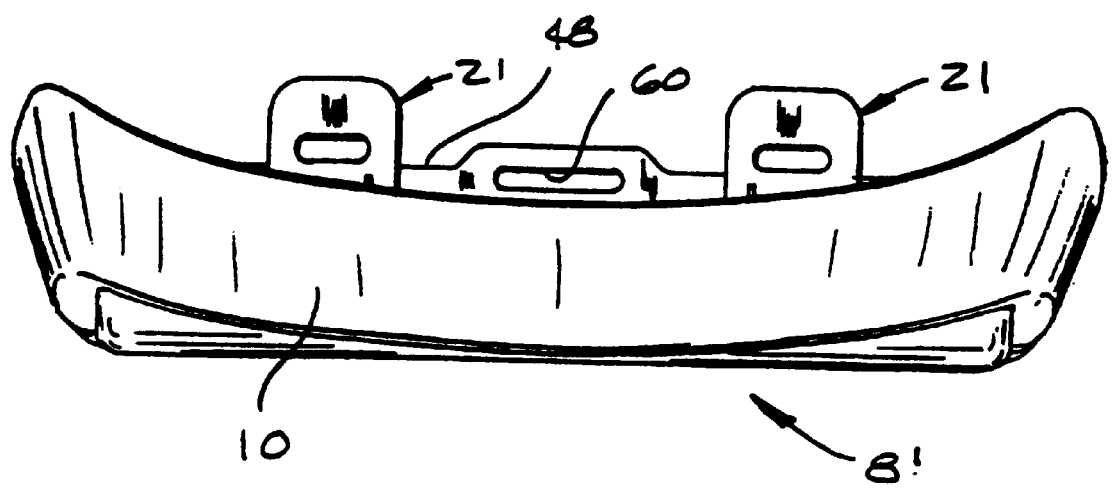
FIG. 14H is a top view of the lens holder of FIG. 14E.
Figure 14M:
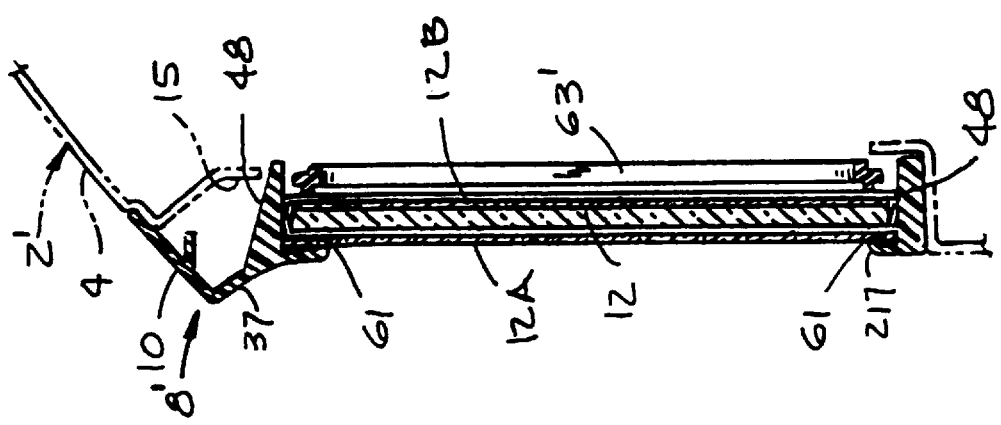
FIG. 14M is a vertical sectional view taken on line 14M—14M of FIG. 1F.

As shown in FIGS. 14G and 14H, the snap fastening elements 21' on the lens holder 8' are somewhat different in construction and location compared to the ramped catches 52 of the lens holder 8. These fastening elements 21' are configured as resilient cantilever members designed to deflect in an upward direction as they pass though apertures 19 in the platform 15 of the shell 2'. After reaching the desired position, locking lugs 471 on the shell snap into openings 473 in the cantilever members 21' to lock the holder 8' in place (FIG. 14K.) The lens holder 8' can be removed from the shell by deflecting the cantilever members up until they are disengaged from the locking lugs 471, and then pivoting the lens holder away from the shell. Additional reinforcements 465 on the rear face of the front panel 37 are provided adjacent the upper end of the holder.

The lens holder 8' illustrated in FIGS. 14E–14M is equipped with a filter lens plate 12, a cover lens plate 12A forward of the filter lens plate for protecting the filter lens plate, and a safety lens plate 12B of shatter resistant material behind the filter lens plate 12. All three lens plates are held in place by a rectangular leaf spring 63' similar to spring 63, except that the upper projection 62' on the lens spring is formed with a hook 62A for hooking through the opening in the lens mount 48 for more securely holding the lens plates in position.

The lens holder 8 (8') is the part of helmet 1 most subject to damage from spatter and other welding discharges. Accordingly, it is, in this embodiment, constructed from nylon, which is resistant to such damage, and which has a nominal wall thickness of 2 mm. The helmet shell 2 is also produced from similar nylon, although a nominal wall thickness of 1.5 mm is used. Notwithstanding the reduced wall thickness of the shell 2, it is shaped to provide sufficient strength for welding applications. The shell is very lightweight to enhance user comfort. Moreover, the helmet shell 2 and lens holder 8 (8') are produced by moulding. The helmet shell is shaped such that no sliders are required during the moulding process.

In other embodiments different wall thicknesses are used, as required.

Figure 8:
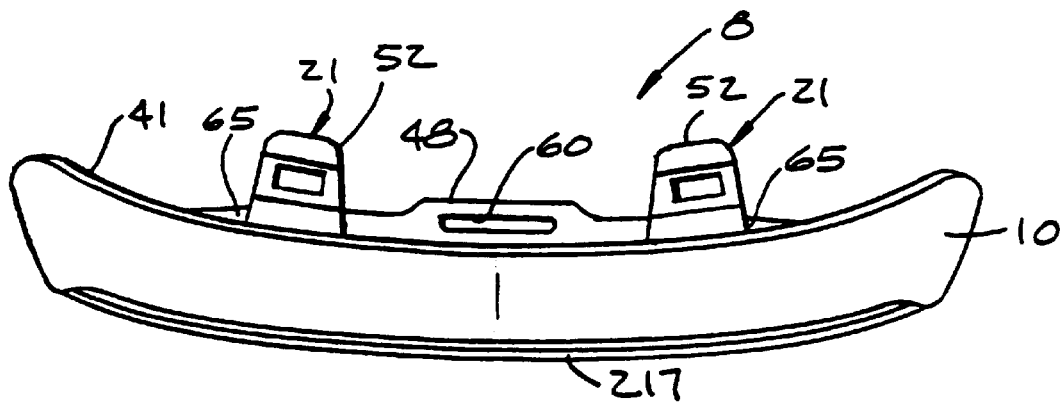
FIG. 8 is a top view of the lens holder of FIG. 6.
Figure 9:
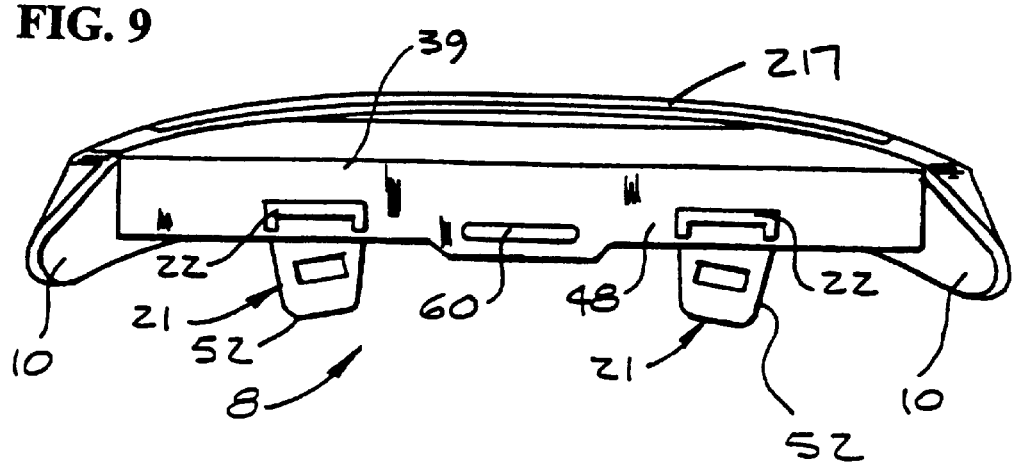
FIG. 9 is a bottom view of the lens holder of FIG. 6.

Clearly, the most critical feature of a welding helmet is the lens plate, and in the event a lens plate is not functioning sufficiently well, the helmet is immediately unusable. A helmet according to the present invention, however, need not be discarded, since it is only necessary to replace the lens holder 8 (8') or indeed only the lens plate 12. Moreover, other cleaning and repair of the lens plate and shell is facilitated due to the ease at which the relevant parts can be disassembled. This advantage of the invention is further due to recesses 65 in one of opposing walls 48 of the lens mount, as best shown in FIG. 8. These recesses 65 allow a user to easily remove the spring 63 by pushing the spring downwardly with respective fingers inserted into recesses 65 to remove projection 62 on the spring from its aperture 60.

In some embodiments, the lens holder 8 (8') has a lens-holding configuration large enough to accommodate a nominal 133×114 mm (5×4 in.) lens plate. Other alternative lens holders are configured to mount smaller lens plates. As such, an operator can select between one of a plurality of lens plates for any specific application. For example, an operator can carry a holder having a 133×114 mm (5×4 in.) lens plate, a second holder having a 83×108 mm (2×4 in.) lens plate embodied in a lift-front format, and a third holder having a 83×108 mm (2×4 in.) lens plate in a fixed-front format.

In other embodiments, the smaller lens plate is mounted in a frame which has dimensions which correspond to the 133×114 mm. (5×4 in.) lens.

Other lens plate sizes are also accommodated by the present invention, which include, without limitation lens plates having the following nominal dimensions: 75×98 mm; 100×90 mm; 60×110 mm; 100×120 mm; 84×109 mm; 50×105 mm; and 51×108 mm.

Because the skirt 10 on the lens holder 8, 8' overlaps the rim 45 on the helmet shell 2, 2' the helmet is resistant to the ingress of spatter and other discharges. This effect is increased due to the outer surface of the skirt 10 being flush with the exterior surface 4 of the helmet shell 2, 2'. In other embodiments the skirt overlaps surface 4 to a greater extent.

The use of fastening elements 21, 22 allows helmet 1 to be narrower and indeed more aesthetically appealing than prior art arrangements.

The telescoping overlap fit between the lens holder 8 (8') and shell 2 (2') provides an improved light seal between the holder and shell as well as improved impact properties. The latter is important to provide protection to the operator and to satisfy standards such as those specified in ANISZ87.1 1989.

Figure 15:
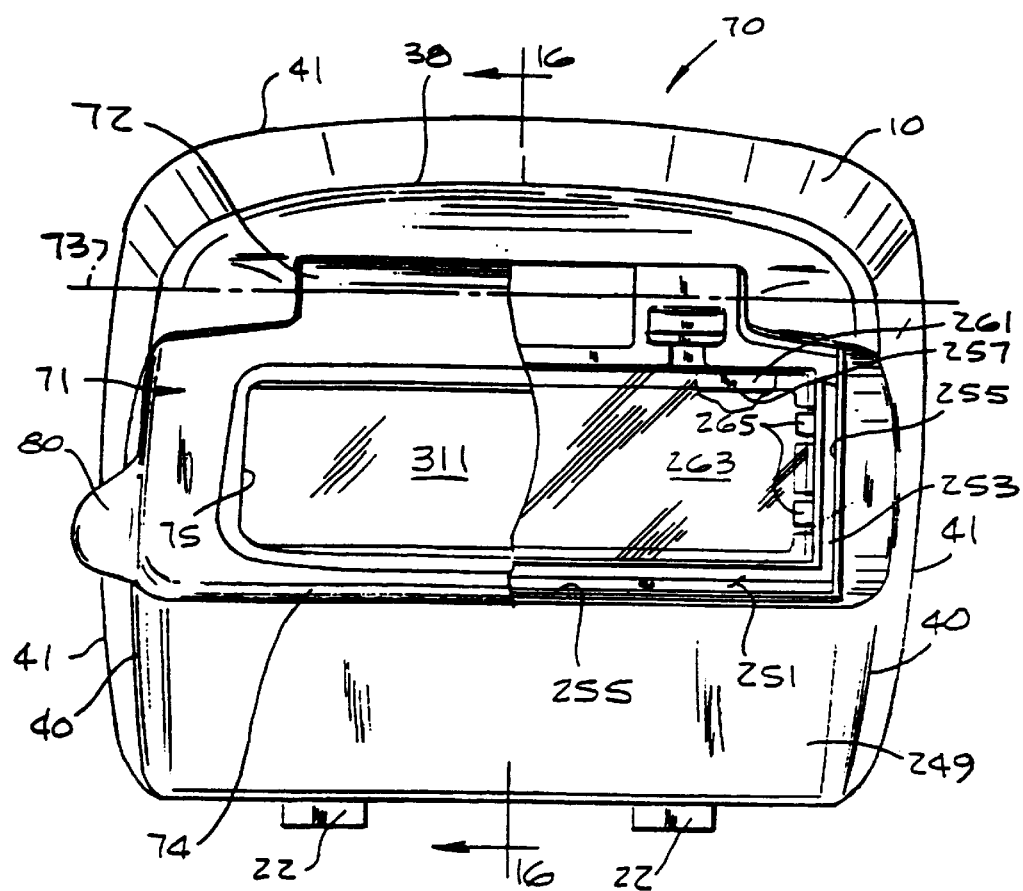
FIG. 15 is a front view of a lift-front lens holder according to the present invention, parts of the lens holder being broken away to illustrate details.
Figure 15A:
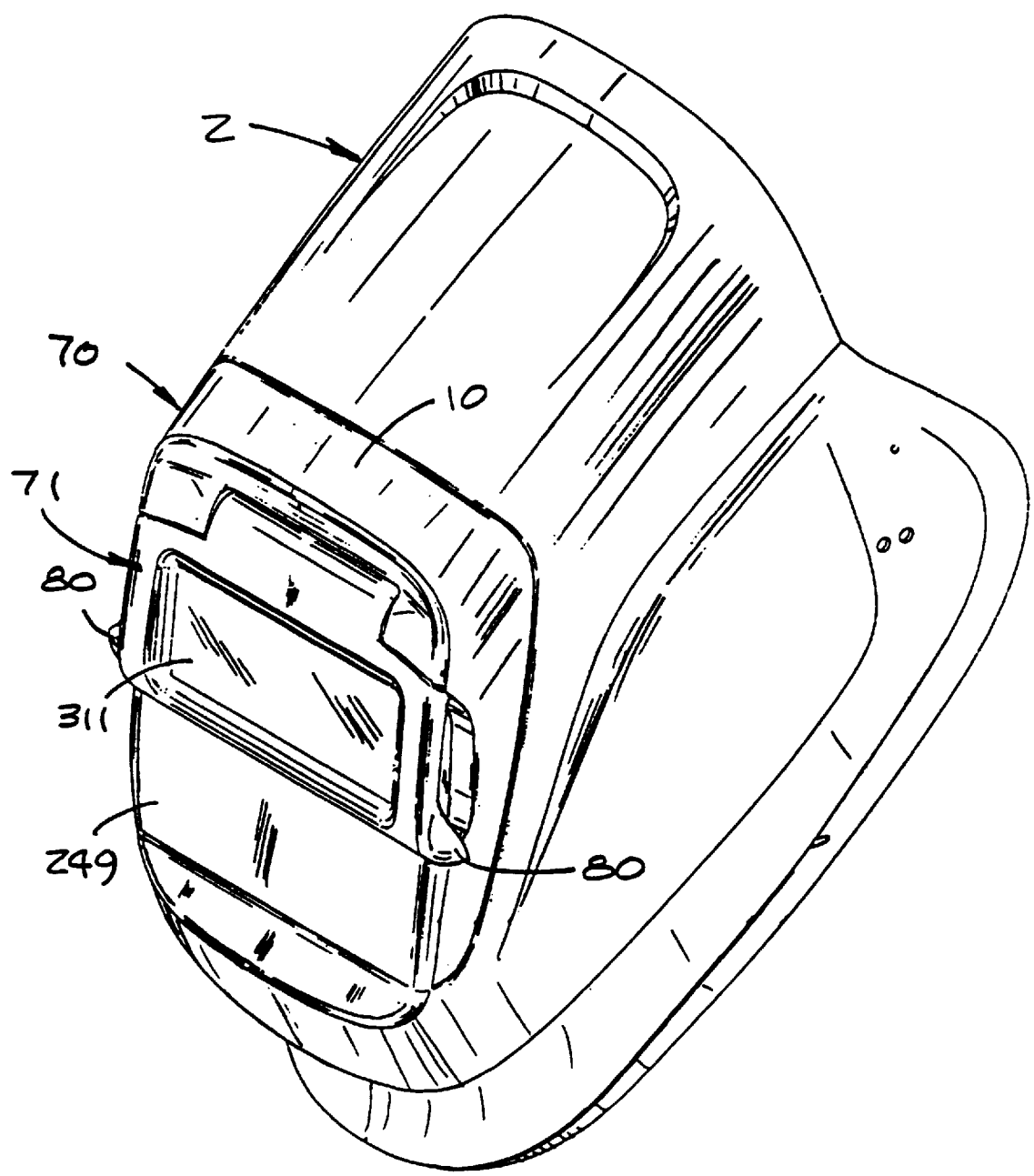
FIG. 15A is a perspective view of the lens holder of FIG. 15 mounted on a helmet shell.
Figure 15B:
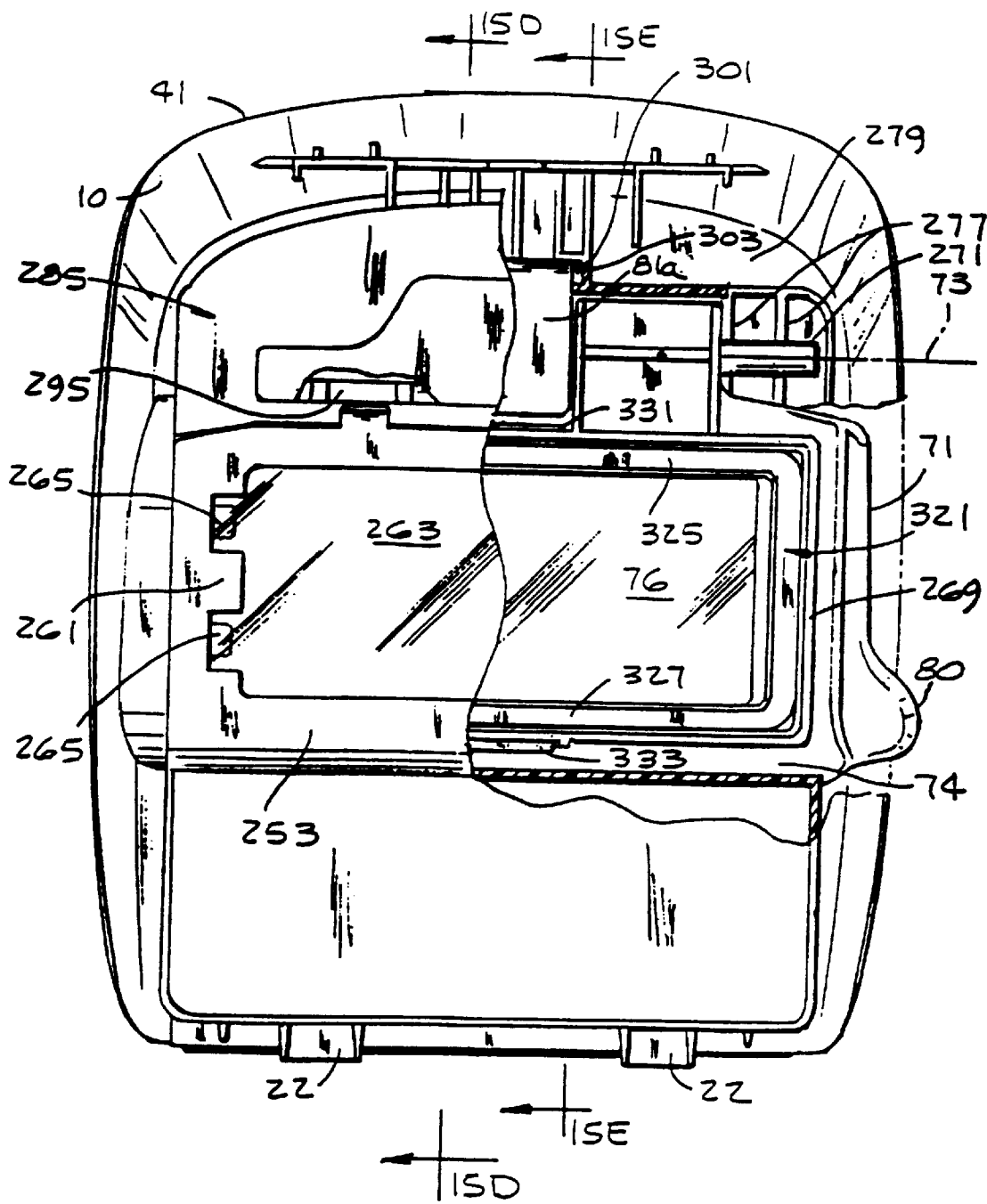
FIG. 15B is a rear view of the lens holder of FIG. 15, parts of the back wall of the lens holder being broken away to illustrate details.

Reference is now made to FIGS. 15, 15A–H and 16 which illustrate a lens holder 70 having a lift-front lens configuration. Lens holder 70 has overall dimensions and an outline substantially the same as that of lens holder 8 (8'), and is intended for similar selective attachment to the helmet shell 2 (2'), as shown in FIG. 15A. That is, holders 8 (8') and 70 are interchangeable and mountable on the same helmet shell. To this end, holders 8 (8') and 70 have mounting systems (e.g., fastening elements 21 and 22) which are of similar configuration. Also, the peripheral skirts 10 on the holders are of essentially identical configuration so that they have the same overlapping telescoping fit with rim of the helmet shell.

Figure 15C:
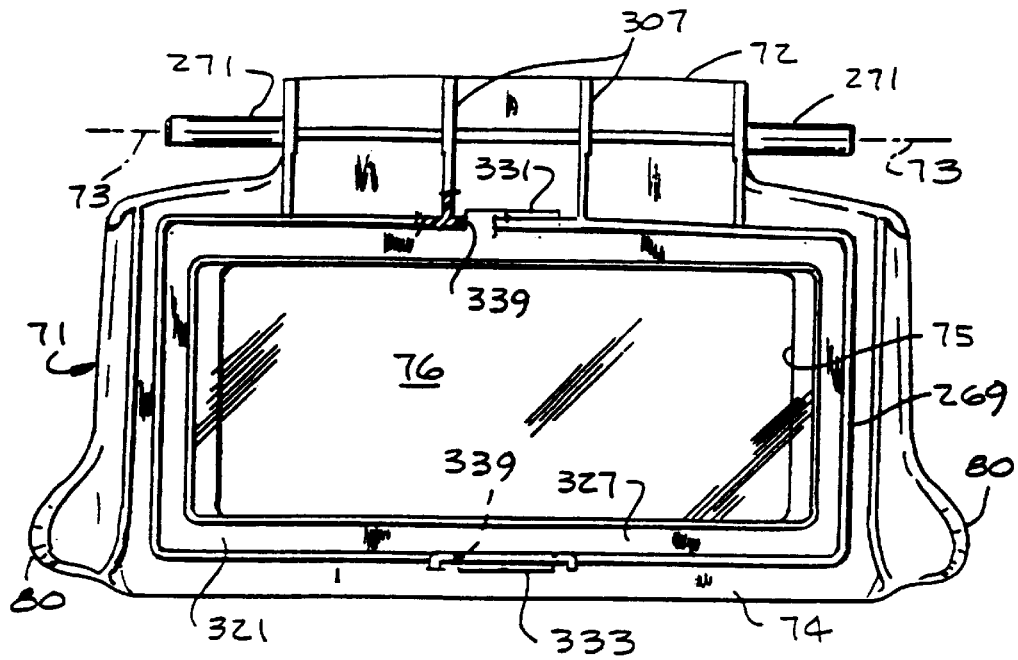
FIG. 15C is a rear view of the lift-front frame of the lens holder of FIG. 15.
Figure 15G:
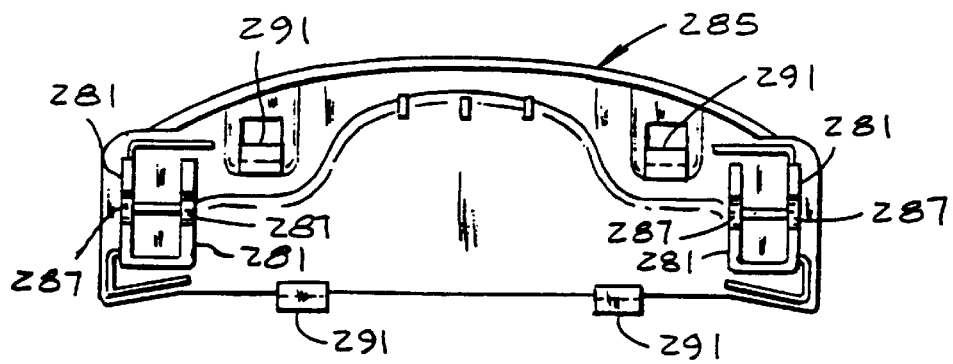
FIG. 15G is an elevational view of the front of the removable back wall portion of the lens holder.
Figure 15H:
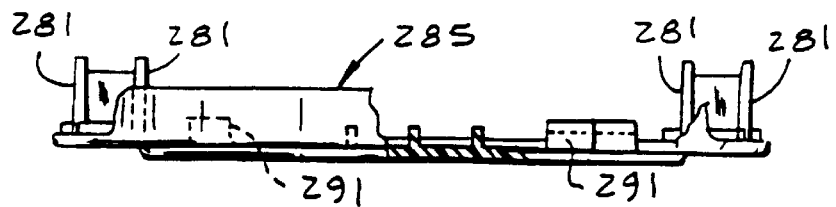
FIG. 15H is a top view of the removable back wall portion with parts broken away to show details.
Figure 16:
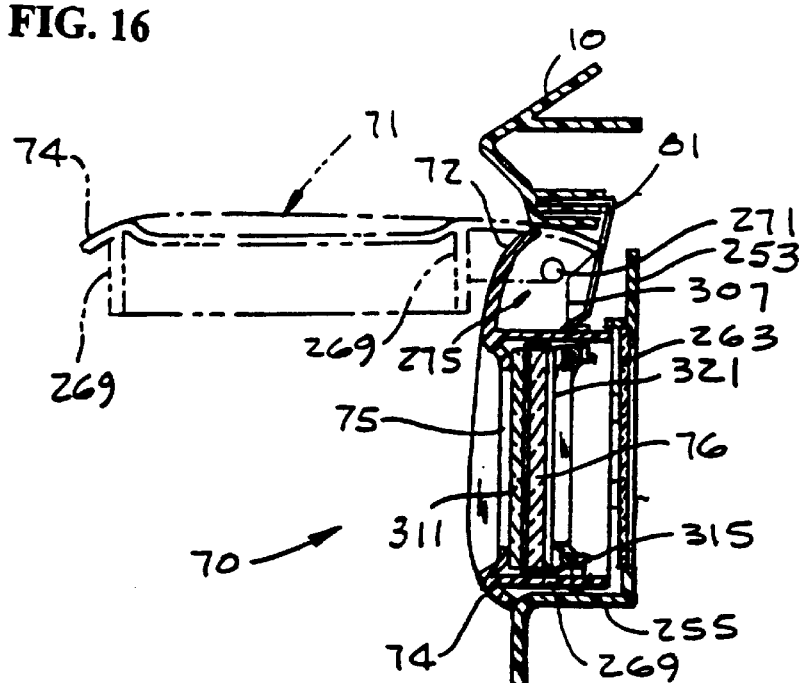
FIG. 16 is a vertical cross section taken along line 16—16 of FIG. 15.

Lens holder 70 is a "lift front" holder which, as illustrated in FIG. 15, includes a front panel 249 having a recessed portion 251 defined by a back wall 253 and four side walls 255 extending forward from the back wall, a lens opening 257 in the back wall, and a lens seat 261 around the lens opening engageable by a safety lens plate 263 held against the lens seat 261 in alignment with the opening 257 by a plurality of retaining members 265 on the back wall. The holder further comprises a flip-up frame 71 having an upper part 72, a lower part 74 and a window opening 75 between the upper and lower parts. The frame has a rectangular lens mount 269 (FIGS. 15B and 15C) on its rear face for holding a filter lens plate 76 which covers the window opening 75 for attenuating light. The frame 71 is hingedly mounted adjacent its upper end 72 to the holder 70 for pivotal movement about an axis 73 between a filtering (operative) position in which the filter lens plate 76 is generally aligned with the safety lens plate 263, the lens opening 257 in the back wall 253 of the holder, and the opening 7 in the helmet shell 2, and a non-filtering (open) position in which the filter lens plate is swung up out of alignment with the openings 7, 257, as illustrated in FIG. 16. The rectangular lens mount 269 on the rear of the frame 71 is configured for a nested fit within the recessed portion 251 of the front panel 249 to provide a light seal when the frame 71 is in its operative position, as illustrated in FIG. 16 in unbroken lines.

The frame 71 is mounted for pivotal movement between its filtering and non-filtering positions by a pair of pivot shafts or trunnions 271 projecting laterally outwardly from opposite sides of the upper part 72 of the frame along axis 73. These trunnions are rotatable in bearings, generally designated 275 (FIG. 15D) in the lens holder 70. The bearing 275 for each trunnion 271 comprises a first bearing part in the form of at least one and preferably two laterally spaced bearing members 277 affixed to a rear face 279 of the front panel 249 (FIGS. 15B and 15D), and a second bearing part in the form of at least one and preferably two bearing members 281 affixed to a removable portion 285 of the back wall 253 of the recessed portion 251 of the front panel 249 (see FIGS. 15D and 15G). As best shown in FIG. 15D, where the lift-front frame 71 is removed for clarity, each bearing member 277, 281 is formed with a shaped (e.g., part-round) bearing surface 287. The design is such that when the removable back wall portion 285 is secured to the holder in a closed position, the bearing members 281 on the back wall cooperate with the bearing members 277 on the front panel 249 to form two complete functional bearings for the trunnions 271. This cooperation is shown in FIG. 15D, where it will be observed that the arcuate bearing surfaces 287 of the bearing members 277 on the front panel 249 are defined by 287 of bearing members 281 on the removable portion 285 of the back wall 253 are defined by recesses which open in a generally forward direction. It will be understood, therefore, that when the removable portion of the back wall is in its installed (closed) position on the holder, the trunnions 271 are held rotatably captive in respective bearings 275. However, when the removable back wall portion 285 is moved away from the holder to an open position, the trunnions 271 may be freely moved out of the bearings 275 to facilitate assembly and disassembly of the frame 71 and the front panel 249 of the holder.

The removable back wall portion 285 of the holder is releasably secured in its closed position by a latching system comprising a plurality of latching elements 291 (FIGS. 15D, 15G and 15H) releasably engageable with cooperable elements comprising recessed formations 295 on the fixed portion of the back wall 253 of holder (FIGS. 15B–15H). Other mechanisms may be used for releasably securing the removable portion of the back wall in its closed position. It will also be noted that when the lens holder 70 is installed on the helmet shell 2, the back wall 253 of the recessed portion of the front panel is positioned closely adjacent the platform 15 at the front of the helmet shell 2, thereby further ensuring that the removable portion of the back wall cannot move away from its closed position during a welding operation. No other fasteners are required to hold the removable back wall portion 285 in place, thus reducing cost and assembly time.

Frame 71 is toggled between its filtering position and its non-filtering position, as shown by way of the broken lines in FIG. 16, by rotating the frame about axis 73. This rotation is initiated by a user manually pushing forward on either or both of two flanges 80 projecting laterally from opposite sides of the frame. Once so initiated, the rotation is assisted by an overcenter spring mechanism comprising at least one leaf spring plate 81 having an upper part 81a releasably held in a slot 301 in a spring retainer 303 affixed to the rear face 279 of the front panel of the holder (see FIGS. 15B and 15E.) The spring plate 81 has a downwardly and forwardly angled lower part 81b which is engageable by a pair of cams 307 affixed to the back of the upper part 72 of the hinged frame. The cams 307 are contoured and profiled to wipe against the lower part 81b of the leaf spring plate 81 to provide an over-center biasing force which assists rotation of frame 71 in both directions (i.e., toward both the filtering and non-filtering positions shown in FIGS. 15E and 15F, respectively). The leaf spring plate 81 and cams 307 may have other configurations without departing from the scope of this invention. For example, two leaf springs at opposite sides of the frame 71 may be used. When in its closed position, the removable back wall portion 285 of the holder holds the spring plate 81 in its operative position with the upper part 81a of the spring received in the slot 301 in the spring retainer 303 (see FIG. 15D). When the back wall portion 285 is moved away, the spring plate 81 may be slidably installed in the retainer.

To reduce the number of separate parts involved, the spring retainer 303, the first bearing part (bearing members 277) and the front panel 249 of the holder 71 are preferably moulded as an integral unit. The flip-up frame 71, cams 307 and trunnions 271 are preferably moulded as a separate integral unit. Finally, the removable back wall portion 285 and the second bearing part (bearing members 281) are preferably moulded as an integral unit. Of course, the number of separate parts may vary.

The lift-front lens holder 70 may also be equipped with a transparent cover lens plate 311 held within the lens mount 269 of the frame 71 forward of the filter plate. As illustrated in FIG. 15E, the cover lens plate and filter lens plate are preferably separated by a spacer 315.

Figure 16A:
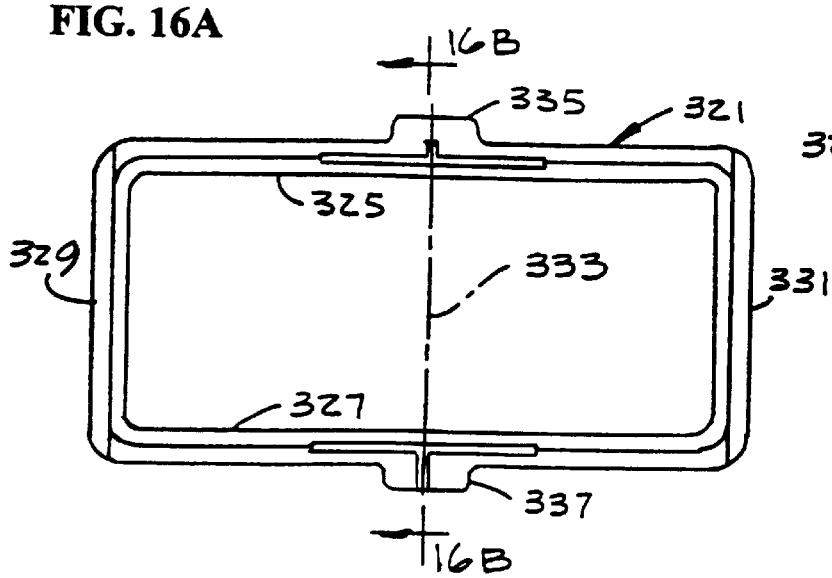
FIG. 16A is a front view of a lens spring for holding a lens plate in place in the lens holder.
Figure 16B:
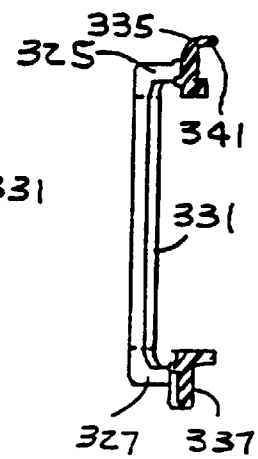
FIG. 16B is a left end view of the lens spring shown in FIG. 16A.
Figure 16C:
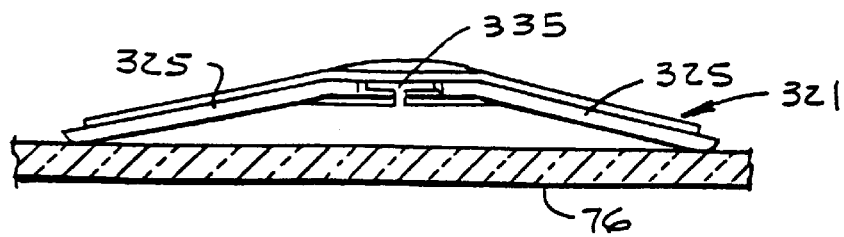
FIG. 16C is a top view of the lens spring of FIG. 16A in a relaxed condition immediately prior to installation of the spring in the lens holder.
Figure 16D:
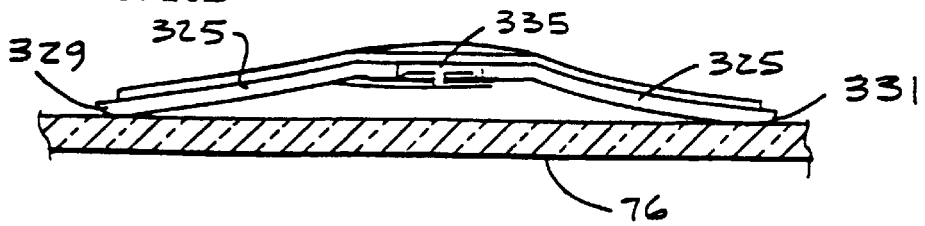
FIG. 16D is a view similar to FIG. 16C but showing the lens spring in a deflected position as installed in the lens holder.

FIGS. 16A–16D show a lens spring, generally designated 321, for holding the filter lens plate 76 and cover plate 311, if used, within the lens mount 269 of the frame. As illustrated, lens spring 321 is a generally rectangular spring having bowed relatively long upper and lower spring members 325, 327 connected by substantially straight shorter side spring members 329, 331, the spring being bowed symmetrically about the central vertical axis 333 of the spring. Upper and lower locking tabs indicated at 335 and 337, respectively, project from the upper and lower spring members generally at the centers of the spring members for reception in openings 339 in the lens mount 269, as shown in FIG. 15C. When the spring 321 is installed in the lens mount with the locking tabs 335, 337 in respective openings 339, the spring deflects to assume a more flattened (but still bowed) configuration, as shown in FIG. 16D, in which the side spring members 329, 331 press against the filter lens plate 76 adjacent opposite sides of the plate to hold it against the frame 71. The upper locking tab 335 is formed with a hook 341 for hooking through a respective opening 339. This arrangement securely holds the spring in place and provides for an efficient distribution of impact force in the event there is an impact against the front surface of the lens plate.

The dimensions of lens spring 321 will vary, depending on the size of the lens plate(s) being held. The important point is that the spring be sized so that it engages the lens plate close to its outer periphery so that the spring does not obstruct the view of the person wearing the helmet.

Figure 17:
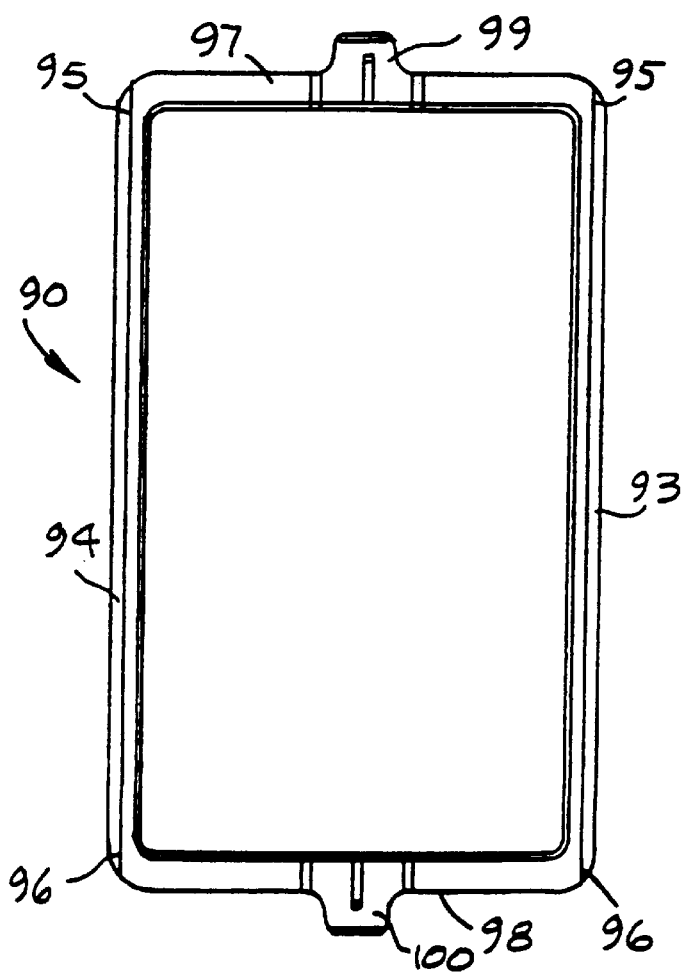
FIG. 17 is a front elevation of a 5×4 in. lens spring for holding a lens plate in place in the lens holder.
Figure 18:
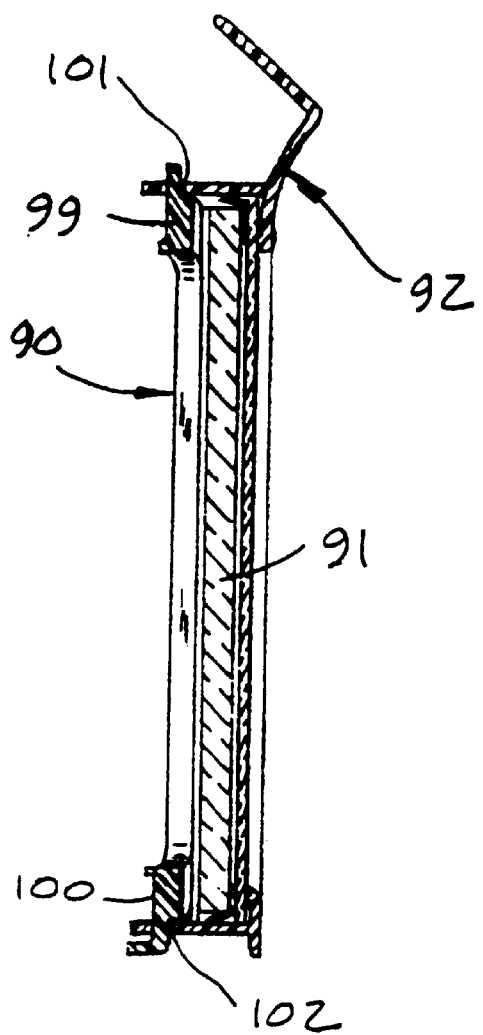
FIG. 18 is a vertical cross section taken along the centerline of an assembly including the lens spring of FIG. 17.
Figure 19:
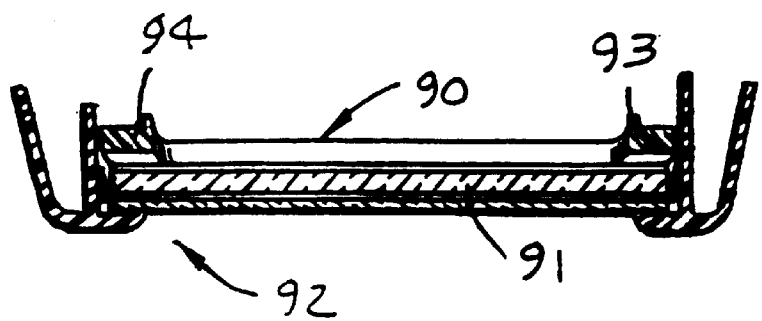
FIG. 19 is a horizontal cross section taken along the centerline of an assembly including the lens spring of FIG. 17.

Reference is now made to FIGS. 17 to 19 which illustrates a rectangular spring 90, which is similar to spring 63, for retaining a lens plate 91 in a lens holder 92. Spring 90 includes two opposed longitudinal co-extending members 93, 94 which have respective ends 95 and 96. In use, members 93 and 94 lie flat against lens plate 91 at or adjacent to its periphery.

Respective opposed ends 95 and 96 are joined by a pair of generally bowed members 97 and 98 which, in use, extend rearwardly away from lens 91. These members include respective engagement formations 99 and 100 in the form of locking is tabs which are received within complementary engagement formations, in the form of apertures (recesses) 101 and 102, in the lens holder. When formations 99 and 100 are within respective apertures 101 and 102, they bias members 93 and 94 into engagement with lens plate 91 which is in turn biased into engagement with the holder.

Spring 90 not only effectively secures lens 91 within holder 92, but allows for easy removal of that lens for cleaning, repair, replacement or the like. More particularly, to remove lens 91, a user applies a force to member 97 sufficient to remove the formation 99 from aperture 101. Spring 90 is then hinged about formation 100, which is still retained within aperture 102, so that once the force is released from member 97 the formation 99 will not rest within aperture 101. The spring is then easily manoeuvred to remove formation 100 from aperture 102. Lens plate 91 is then removed for whatever purpose. Replacement of the lens plate(s) within the holder is carried out in the reverse order to the steps for removal described above.

Figure 20:
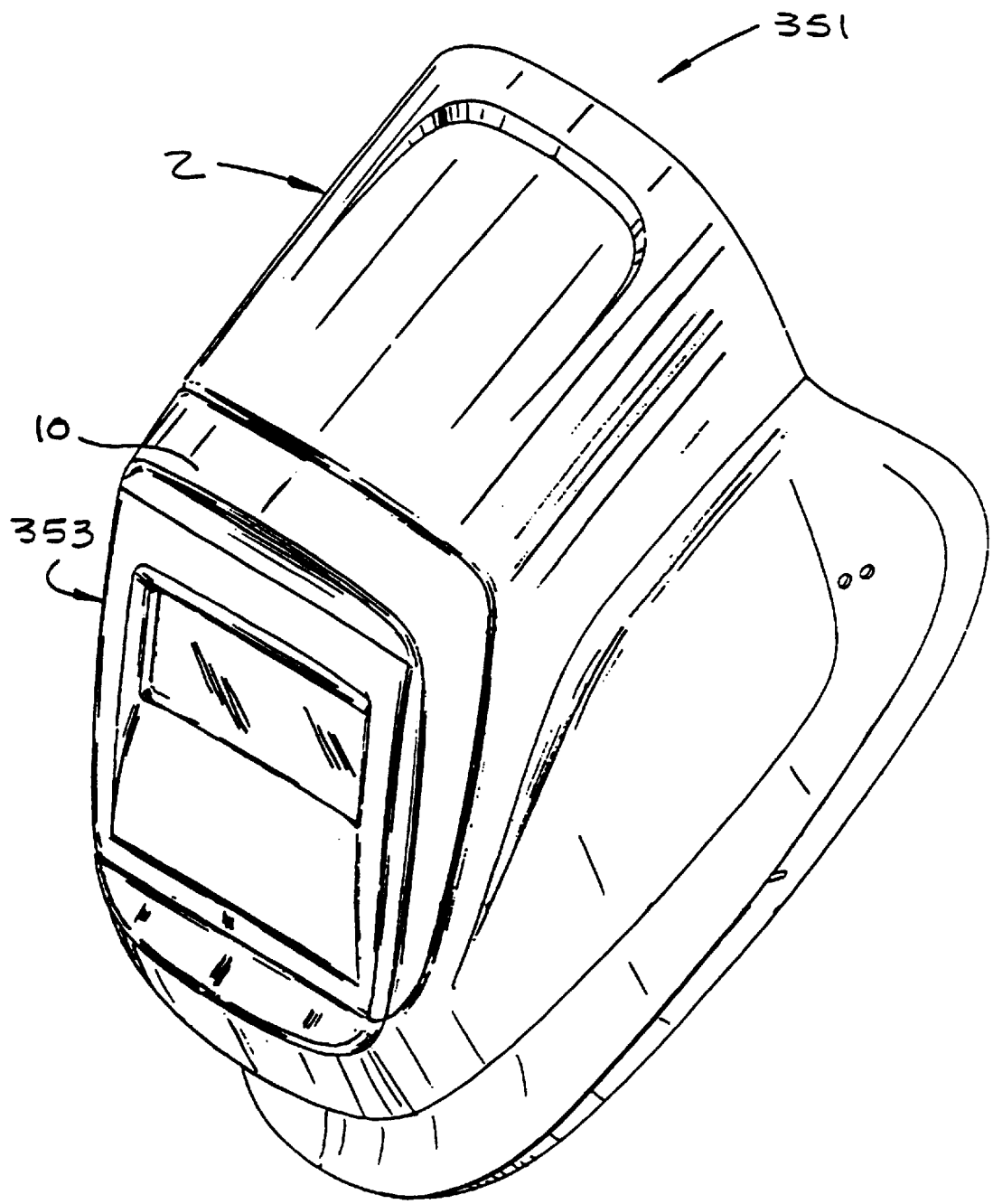
FIG. 20 is a perspective view of a helmet having a lens holder with fixed-front configuration for holding a lens of different size than the fixed-front lens holder of FIG. 1.

FIG. 20 shows a helmet 351 very similar to helmet system 1 and corresponding parts are identified by corresponding reference numerals. The major difference is that the helmet is a fixed-front helmet having a lens holder 353 configured for holding a set of one or more 2×4 in. lens plates (e.g., a cover plate and filter plate).

It will be observed from the foregoing that the helmet system of the present invention provides many advantages. One important advantage is that the helmet system permits lens holders having different styles (e.g., fixed front and flip-front) and/or lens sizes to be mounted on the same helmet shell. Thus, if a user wishes to change lens sizes or styles, the user simply removes the first lens holder from the helmet shell, selects a second lens holder of the desired configuration, and mounts the second lens holder on the helmet in the manner described above. This can be accomplished quickly and easily using the snap-in fastening system of the present invention. Similarly, a lens holder may be readily removed so that the cover and/or safety and/or filter lens plate(s) can be replaced when necessary.

Another advantage of the helmet system of the present invention is the unique mag lens mounting system which enables a mag lens plate to be mounted at the appropriate height and location relative to the opening in the helmet shell, depending on the preference of the user, the configuration of the lens holder, the type of work being done, etc.

Still another advantage of the present invention is the unique leaf spring mechanism used in the flip-front style helmet. The unique design minimises the number of parts involved, thereby reducing production and assembly costs.

Although the invention has been described with reference to a specific example, it will be appreciated by those skilled in the art that it may be embodied in many other forms.

What is claimed is:

1. A light shielding helmet system comprising:

a helmet shell configured for placement on the head of a user, said helmet shell having an opening therein at a front of the shell for providing said user with a field of vision beyond the helmet, and a rim around the shell opening;

a first lens holder having a first lens-holding configuration for holding a first set of one or more lens plates, said first lens holder being releasably mountable on the helmet shell in a working position in which the first lens holder engages the rim of the helmet shell, in which the first lens holder is disposed in front of the shell opening, and in which the one or more lens plates held by the first lens holder are generally aligned with the shell opening;

a second lens holder having a second lens-holding configuration different from said first lens-holding configuration of the first lens holder for holding a second set of one or more lens plates, said second lens holder being releasably mountable on the helmet shell in a working position in which the second lens holder engages the rim of the helmet shell, in which the second lens holder is disposed in front of the shell opening, and in which the one or more lens plates held by the second lens holder are generally aligned with said shell opening; and a mounting system on said first and second lens holders and said helmet shell which enables reach lens holder to be releasably mounted on said helmet shell so that the first and second lens holders can be used interchangeably with the same helmet shell, said mounting system comprising one or more snap-fastening elements on each of said first and second lens holders which are cooperable with one or more snap-fastening elements on said helmet shell to releasably fasten either one of said lens holders in its said working position on the helmet shell.

2. A helmet system as set forth in claim 1 wherein each of said first and second lens holders is configured for a telescoping fit on the rim of the helmet shell.

3. A helmet system as set forth in claim 1 wherein each of said first and second lens holders has a peripheral skirt configured for an overlapping telescoping fit with the rim of the helmet shell when the lens holder is in said working position, the peripheral skirts of said first and second lens holders having substantially identical configurations so that both lens holders have the same fit with said helmet shell.

4. A helmet system as set forth in claim 1 wherein each of said first and second lens holders is configured for holding a safety lens plate in a fixed position and a filter lens plate forward of the safety lens plate, said first lens holder further comprising a frame holding said filter lens plate, said frame being pivoted on the lens holder for movement between a filtering position in which the filter lens plate is generally aligned with the fixed safety lens plate and said shell opening, and a non-filtering position in which the filter lens plate is away from the fixed safety lens plate and out of alignment with the shell opening.

5. A helmet system as set forth in claim 4 wherein said first lens holder has a recessed portion, a lens opening in the recessed portion, a seat around the lens opening engageable by said safety lens plate, and a system for releasably holding the safety lens plate on the lens seat generally in alignment with the lens opening.

6. A lens system as set forth in claim 5 wherein the recessed portion of the first lens holder is defined by a back wall bounding said lens opening and side walls extending forward from the back wall, said frame being so configured that when it is in its said filtering position, the frame nests within said recessed portion.

7. A light shielding helmet system comprising:
a helmet shell configured for placement on the head of a user, said helmet shell having an opening therein at a front of the shell for providing said user with a field of vision beyond the helmet, and a rim around the shell opening;
a first lens holder having a first lens-holding configuration for holding a first set of one or more lens plates, said first lens holder being releasably mountable on the helmet shell in a working position in which the first lens holder engages the rim of the helmet shell, in which the first lens holder is disposed in front of the shell opening, and in which the one or more lens plates held by the first lens holder are generally aligned with the shell opening; and
a second lens holder having a second lens-holding configuration different from said first lens-holding configuration of the first lens holder for holding a second set of one or more lens plates, said second lens holder being releasably mountable on the helmet shell in a working position in which the second lens holder engages the rim of the helmet shell, in which the second lens holder is disposed in front of the shell opening, and in which the one or more lens plates held by the second lens holder are generally aligned with said shell opening;
each of said first and second lens holders having a mounting system which enables the lens holder to be releasably mounted on said helmet shell so that the first and second lens holders can be used interchangeably with the same helmet shell, and wherein said first lens-holding configuration is a fixed-front configuration sized for holding one or more lens plates of a first size in length and width, and said second lens-holding configuration is a fixed-front configuration sized for holding one or more lens plates of a second size in length and width different from said first size.

8. A helmet system as set forth in claim 7 wherein said mounting system of each of said first and second lens holders comprises one or more fastening elements which are cooperable with one or more fastening elements on the helmet shell to releasably fasten the lens holder in its said working position on the helmet shell, said one or more fastening elements on said first lens holder having the same configuration and location as the one or more fastening elements on said second lens holder so that said first and second lens holders can be used interchangeably with said helmet shell.

9. A lens system for use with a single light shielding helmet shell configured for placement on the head of a user, said helmet shell having an opening therein at a front of the shell for providing said user with a field of vision beyond the helmet, and a rim around the shell opening, said lens system comprising:
a first lens holder having a first lens-holding configuration for holding a first set of one or more lens plates, said first lens holder being releasably mountable on the helmet shell in a working position in which the first lens holder engages the rim of the helmet shell, in which the first lens holder is disposed in front of the shell opening, and in which the one or more lens plates of the first set are generally aligned with said shell opening;
a second lens holder having a second lens-holding configuration different from said first lens-holding configuration for holding a second set of one or more lens plates, said second lens holder being releasably mountable on the helmet shell in a working position in which the second lens holder engages the rim of the helmet shell, in which the second lens holder is disposed in front of the shell opening, and in which the one or more lens plates of the second set are generally aligned with said shell opening; and
a mounting system on said first and second lens holders and said helmet shell which enables each lens holder to be releasably mounted on said helmet shell so that the first and second lens holders can be used interchangeably with the same helmet shell, said mounting system comprising one or more snap-fastening elements on each of said first and second lens holders which are cooperable with one or more snap-fastening elements on said helmet shell to releasably fasten either one of said lens holders in its said working position on the helmet shell.

10. A lens system as set forth in claim 9 wherein said first lens-holding configuration is a fixed-front configuration and said second lens-holding configuration is a lift-front configuration.

11. A lens system as set forth in claim 9 wherein each of said first and second lens holders has a peripheral skirt configured for an overlapping telescoping fit with the rim of the helmet shell, the peripheral skirts of said first and second lens holders having substantially identical configurations so that both lens holders have the same fit with said helmet shell.

12. A lens system as set forth in claim 9 wherein each of said first and second lens holders is configured for holding a safety lens plate in a fixed position and a filter lens plate forward of the safety lens plate, said first lens holder further comprising a frame holding said filter lens plate, said frame being pivoted on the lens holder for movement between a filtering position in which the filter lens plate is generally aligned with the fixed safety lens plate and said shell opening, and a non-filtering position in which the filter lens plate is away from the fixed safety lens plate and out of alignment with the shell opening.

13. A lens system as set forth in claim 12 wherein said first lens holder has a recessed portion, a lens opening in the recessed portion, a seat around the lens opening engageable by said safety lens plate, and a system for releasably holding the safety lens plate on the seat generally in alignment with the lens opening.

14. A lens system as set forth in claim 13 wherein the recessed portion of the first lens holder is defined by a back wall bounding said lens opening and side walls extending forward from the back wall, said frame being so configured that when it is in its said filtering position, the frame nests within said recessed portion.

15. A lens system for use with a single light shielding helmet shell configured for placement on the head of a user, said helmet shell having an opening therein at a front of the shell for providing said user with a field of vision beyond the helmet, and a rim around the shell opening, said lens system comprising:

a first lens holder having a first lens-holding configuration for holding a first set of one or more lens plates, said first lens holder being releasably mountable on the helmet shell in a working position in which the first lens holder engages the rim of the helmet shell, in which the first lens holder is disposed in front of the shell opening, and in which the one or more lens plates of the first set are generally aligned with said shell opening; and a second lens holder having a second lens-holding configuration different from said first lens-holding configuration for holding a second set of one or more lens plates, said second lens holder being releasably mountable on the helmet shell in a working position in which the second lens holder engages the rim of the helmet shell, in which the second lens holder is disposed in front of the shell opening, and in which the one or more lens plates of the second set are generally aligned with said shell opening;

each of said first and second lens holders having a mounting system which enables the lens holder to be releasably mounted on said helmet shell so that the first and second lens holders can be used interchangeably with the same helmet shell, and wherein said first lens-holding configuration is a fixed-front configuration sized for holding one or more lens plates of a first size in length and width, and said second lens-holding configuration is a fixed-front configuration sized for holding one or more lens plates of a second size in length and width different from said first size.

16. A helmet system as set forth in claim 15 wherein said mounting system of each of said first and second lens holders comprises one or more fastening elements which are cooperable with one or more fastening elements on the helmet shell to releasably fasten the lens holder in its said working position on the helmet shell, said one or more fastening elements on said first lens holder having the same configuration and location as the one or more fastening elements on said second lens holder so that said first and second lens holders can be used interchangeably with said helmet shell.

17. A light shielding helmet comprising:

a moulded plastic helmet shell configured for placement on the head of a user, said helmet shell having a front, top, opposite sides and an exterior surface, an opening in the front of the shell for providing the user with a field of vision beyond the helmet, and a rim projecting forward from the front of the shell around the shell opening, said rim having a top exterior surface and opposite side exterior surfaces recessed relative to the exterior surface of the helmet shell;

first and second lens plates;

a lens holder for holding the first and second lens plates generally parallel to one another with one plate behind the other, and a mounting system for releasably mounting the lens holder on the helmet shell in a working position in which the lens holder has a close fit with the rim of the helmet shell substantially to prevent the passage of light therepast, in which the lens holder is disposed in front of the opening in the helmet shell, and in which the lens plates held by the lens holder are generally aligned with the shell opening;

said lens holder comprising a front panel having top, opposite sides and a bottom, and a peripheral skirt extending rearward from the front panel along its top and opposite sides, said front panel and skirt being formed as a moulded plastic unit, the skirt having an exterior surface;

the skirt of the lens holder being configured to be inserted over the top and opposite sides of the forwardly projecting rim of the helmet shell to mount the lens holder in its said working position, the skirt of the lens holder further being configured to have an overlapping telescoping fit with the exterior surface of the rim so that the exterior surface of the skirt has a substantially flush fit with the exterior surface of the helmet shell to provide a smooth joint between the shell and the rim along the top and opposite sides of the rim.

18. A light shielding helmet as set forth in claim 17 wherein the first lens plate is a safety lens plate and the second lens plate is a filter lens plate forward of the safety lens plate, said lens holder further comprising a frame holding said filter lens plate, said frame being pivoted on the lens holder for movement between a filtering position in which the filter lens plate is generally aligned with the safety lens plate and the opening in the helmet shell, and a non-filtering position in which the filter lens plate is out of alignment with the opening in the helmet shell.

19. A light shielding helmet as set forth in claim 18 wherein the front panel of the lens holder has a recessed portion, a lens opening in the recessed portion, a seat around the lens opening engageable by said safety plate, and a system for releasably holding the safety plate on the seat generally in alignment with the lens opening.

20. A light shielding helmet as set forth in claim 19 wherein the recessed portion of the front panel is defined by a back wall bounding said lens opening therein and side walls extending forward from the back wall, said frame being so configured that when it is in its said filtering position, the frame nests within said recessed portion.

21. A light shielding helmet as set forth in claim 17 wherein said lens holder is a first lens holder configured for holding lenses of a first size in length and width, said helmet further comprising a second lens holder releasably mountable on the helmet shell in said working position and configured for holding lenses of a second size in length and/or width different from said first size.

22. A light shielding helmet as set forth in claim 21 wherein said first and second lens holders are interchangeably mountable on the helmet shell.

23. A light shielding helmet as set forth in claim 17 wherein the skirt on the lens holder has a wall thickness, and wherein the exterior surface of the rim is recessed relative to said exterior surface of the helmet shell by a distance approximately equal to said wall thickness so that when the lens holder is mounted on the rim, the exterior surface of the skirt is flush with the exterior surface of the helmet shell.

24. A light shielding helmet as set forth in claim 17 further comprising a third lens plate held by the lens holder so that the third plate is generally parallel to and in general alignment with the first and second lens plates, the first lens plate being a safety lens plate, the second lens plate being a filter lens plate forward of the safety lens plate, and said third lens plate being a cover plate positioned forward of the safety and filter lens plates, said lens holder further comprising a frame holding said filter lens plate and said cover lens plate, said frame being mounted on the lens holder for movement between a filtering position in which the filter lens plate and cover lens plate are generally aligned with the safety lens plate and the opening in the helmet shell, and a non-filtering position in which the filter and cover lens plates are out of alignment with the opening in the helmet shell.

25. A helmet shell for a light shielding helmet, said shell being configured for placement on the head of a user and having an opening therein at a front of the shell for providing said user with a field of vision beyond the shell, a rim around the opening configured for mounting a lens holder in a position wherein the lens holder is in front of the opening and one or more lens plates held by the lens holder are generally aligned with the opening, and a mounting system on the helmet shell for mounting a magnifying lens plate in a plurality of different positions heightwise with respect to the opening in the shell whereby the heightwise position of the magnifying lens plate may be selectively varied, said mounting system comprising a plurality of lens supports formed integrally with the helmet shell and positioned at different elevations on the inside of the shell adjacent the opening in the helmet shell.

26. A method of changing lens plates in a light shielding helmet, said helmet comprising a helmet shell configured for placement on the head of a user and having an opening at a front of the shell for providing said user with a field of vision beyond the helmet, a rim around the shell opening, and a first lens holder having a first lens-holding configuration releasably mounted in a working position on the shell in front of the opening in the helmet shell in which the first lens holder engages the rim of the shell, said lens holder holding a first set of one or more lens plates in general alignment with the opening in the helmet shell, said lens holder and helmet shell having cooperable snap-fastening elements for releasably mounting the lens holder on the helmet shell, said method comprising the steps of:

removing the first lens holder from the helmet shell by releasing said cooperable snap-fastening elements on the first lens holder and shell and then moving the lens holder away from the shell and off the rim;

selecting a second lens holder having a second lens-holding configuration different from said first lens-holding configuration of the first lens holder for holding a second set of one or more lens plates, said second lens holder having snap-fastening elements cooperable with said elements on the helmet shell; and mounting the second lens holder on the helmet shell in said working position and fastening the cooperable snap-fastening elements so that the second lens holder is disposed in front of the opening In the helmet shell and the one or more lens plates of the second set of lens plates are generally aligned with the opening in the helmet shell.

27. A method as set forth in claim 26 wherein said mounting step comprises moving the second lens holder into a position where it is in a telescoping fit with the rim of the shell substantially to prevent the passage of light therepast.

28. A light shielding helmet comprising:

a helmet shell configured for placement on the head of a user, said helmet shell having an opening therein at a front of the shell for providing said user with a field of vision beyond the helmet;

a lens holder comprising a panel releasably mounted on the helmet shell at the front of the shell and having an opening therein aligned with the opening in the helmet shell, and a frame mounted at the front of the panel for holding a filter lens plate;

a pair of laterally spaced bearings on the panel mounting the frame for pivotal movement about a pivot axis between a filtering position in which the filter lens plate is aligned with the openings in the helmet shell and panel, and a non-filtering position in which the filter lens plate is pivoted away from said openings, said frame having a shaft rotatable in each of said bearings, each bearing comprising a first bearing part affixed to the panel and a second bearing part affixed to a removable part of the panel movable from a closed position in which it is secured to the panel and an open position in which it is away from the panel, said first and second bearing parts being cooperable when the removable part of the panel is in said closed position to form said bearings; and a leaf spring mechanism comprising at least one leaf spring mounted on one of the panel and the frame and at least one cam mounted on the other of the panel and the frame, said cam and leaf spring being engageable with one another as the frame is pivoted between said filtering and non-filtering position to urge the frame toward said filtering position when the frame is adjacent said filtering position and toward said non-filtering position when the frame is adjacent said non-filtering position.

29. A light shielding helmet as set forth in claim 28 wherein said removable part of the panel in said closed position is engageable with the helmet shell.

30. A light shielding helmet as set forth in claim 28 wherein said frame is a moulded part having a pair of integral shafts extending laterally outwardly from opposite sides of the frame adjacent an upper end of the frame, said shafts being rotatable in said bearings.

31. A light shielding helmet as set forth in claim 28 wherein said panel has a recessed portion for receiving said frame when the frame is in said filtering position, said recessed portion comprising a back wall and a plurality of side walls extending forward from said back wall, said removable part of the panel comprising a portion of said back wall.

32. A light shielding helmet as set forth in claim 31 wherein said at least one leaf spring is mounted on the panel and the cam is mounted on the frame.

33. A light shielding helmet as set forth in claim 32 wherein said at least one leaf spring is mounted between the bearings generally midway between opposite sides of the frame.

34. A light shielding helmet as set forth in claim 32 further comprising a spring retainer on a rear face of said panel for releasably holding said leaf spring, said removable part of the panel holding the leaf spring captive in said spring retainer when the removable part of the panel is in its said closed position, and said leaf spring being removable from the spring retainer when the removable part of the panel is in said open position.

35. A light shielding helmet as set forth in claim 34 wherein said spring retainer, said first bearing part and said panel are moulded as an integral unit, and wherein said frame and cam are moulded as a separate integral unit.

36. A light shielding helmet as set forth in claim 35 wherein said removable part of the panel and said second bearing part are moulded as an integral unit.

37. A light shielding helmet as set forth in claim 36 further comprising cooperable latching elements on the removable part of the panel and on said rear face of the panel for releasably latching the removable part of the panel in said closed position.

38. A light shielding helmet as set forth in claim 28 further comprising a lens mount on the frame for holding said filter lens plate, and a lens spring for retaining the filter lens plate in the lens mount, said lens spring comprising a first pair of opposing relatively long spring elements and a second pair of opposing shorter spring elements, the spring elements of said first and second pairs combining to form a rectangular configuration, the two relatively long spring elements of the first pair having bowed shapes and having locking elements thereon engageable with the lens mount to hold the spring in a position in which the bowed spring elements are resiliently deflected to create a force which pushes the filter lens toward the frame to hold it in position.

* * * * *

UNITED STATES PATENT AND TRADEMARK OFFICE
CERTIFICATE OF CORRECTION

PATENT NO. : 6,185,739 B1
DATED : February 13, 2001
INVENTOR(S) : Ivan Verkic et al.

It is certified that error appears in the above-identified patent and that said Letters Patent is hereby corrected as shown below:

Column 14,
Line 67, "reach" should read -- each --.

Signed and Sealed this

Thirteenth Day of December, 2005

JON W. DUDAS
*Director of the United States Patent and Trademark Office*